United States Patent
Khatib

(10) Patent No.: US 10,253,374 B2
(45) Date of Patent: Apr. 9, 2019

(54) NON-INVASIVE ASSAYS FOR EMBRYO QUALITY

(71) Applicant: WISCONSIN ALUMNI RESEARCH FOUNDATION, Madison, WI (US)

(72) Inventor: Hasan Khatib, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/155,068

(22) Filed: May 15, 2016

(65) Prior Publication Data
US 2016/0333427 A1 Nov. 17, 2016

Related U.S. Application Data

(60) Provisional application No. 62/161,894, filed on May 15, 2015.

(51) Int. Cl.
*C12Q 1/68* (2018.01)
*C12Q 1/6888* (2018.01)

(52) U.S. Cl.
CPC ..... *C12Q 1/6888* (2013.01); *C12Q 2600/124* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2008/0241831 A1* 10/2008 Fan ...................... C12Q 1/6844
435/6.16

OTHER PUBLICATIONS

Kropp et al. (Frontiers in Genetics, vol. 5, Article 91, pp. 1-8; published Apr. 24, 2014) (Year: 2014).*
Wang et al. (Mol. BioSyst., 2013, 9, 2154-2162) (Year: 2013).*
Centers for Disease Control and Prevention, American Society for Reproductive Medicine, Society for Assisted Reproductive Technology. 2012 Assisted Reproductive Technology Fertility Clinic Success Rates Report. Atlanta (GA): US Dept of Health and Human Services; 2014.
Chandra A, Copen C, Stephen E: Infertility and Impaired Fecundity in the U.S.-1982-2010 Data from the National Health Survey of Family Growth. National Health Statistics Reports, No. 67, Aug. 2013, pates 1-19.
Lucy MC: ADSA Foundation Scholar Award—Reproductive loss in high-producing dairy cattle: Where will it end? Journal of Dairy Science 2001, 84(6):1277-1293.
Diskin MG, Murphy JJ, Sreenan JM: Embryo survival in dairy cows managed under pastoral conditions. Animal Reproduction Science 2006, 96(3-4):297-311.

2012 Assisted Reproductive Technology Fertility Clinics Success Rates Report. National Center for Chronic Disease Prevention and Health promotion; 2012; 43 pages.
Farin PW, Piedrahita JA, Farin CE: Errors in development of fetuses and placentas from in vitro-produced bovine ambryos. Theriogenology 2006, 65(1):178-191.
Van Soom A, Mateusen B, Leroy J, De Kruif A: Assessment of mammalian embryo quality: what can we learn from embryo morphology? Reprod Biomed Online 2003, 7(6):664-670.
Driver AM, Penagaricano F, Huang W, Ahmad KR, Hackbart KS, Wiltbank MC, Khatib H: RNA-Seq analysis uncovers transcriptomic variations between morphologically similar in vivo- and in vitro-derived bovine blastocysts. Bmc Genomics 2012, 13.
Mitchell PS, Parkin RK, Kroh EM, Fritz BR, Wyman SK, Pogosova-Agadjanyan EL, Peterson A, Noteboom J, O'Briant KC, Allen A et al: Circulating microRNAs as stable blood-based markers for cancer detection. Proceedings of the National Academy of Sciences of the United States of America 2008, 105(30):10513-10518.
Valadi H, Ekstrom K, Bossios A, Sjostrand M, Lee JJ, Lotvall JO: Exosome-mediated transfer of mRNAs and microRNAs is a novel mechanism of genetic exchange between cells. Nature Cell Biology 2007, 9(6):654-U672.
Wang K, Zhang SL, Weber J, Baxter D, Galas DJ: Export of microRNAs and microRNA-protective protein by mammalian cells. Nucleic Acids Research 2010, 38(20):7248-7259.
Chen X, Ba Y, Ma LJ, Cai X, Yin Y, Wang KH, Guo JG, Zhang YJ, Chen JN, Guo X et al: Characterization of -microRNAs in serum: a novel class of biomarkers for diagnosis of cancer and other diseases. Cell Research 2008, 18 (10):997-1006.
Turchinovich A, Weiz L, Langheinz A, Burwinkel B: Characterization of extracellular circulating microRNA. Nucleic Acids Research 2011, 39(16):7223-7233.
Rayner KJ, Hennessy EJ: Extracellular communication via microRNA: lipid particles have a new message. Journal of Lipid Research 2013, 54(5):1174-1181.
Xu L, Yang BF, Ai J: MicroRNA transport: A new way in cell communication. Journal of Cellular Physiology 2013, 228 (8)1713-1719.
Wang ZF, Yao H, Lin S, Zhu X, Shen Z, Lu G, Poon WS, Xie D, Lin MCM, Kung HF: Transcriptional and epigenetic regulation of human microRNAs. Cancer Letters 2013, 331(1):1-10.
Filipowicz W, Bhattacharyya SN, Sonenberg N: Mechanisms of post-transcriptional regulation by microRNAs: are the answers in sight? Nature Reviews Genetics 2008, 9(2):102-114.
Ambros V: The functions of animal microRNAs. Nature 2004, 431(7006):350-355.

(Continued)

*Primary Examiner* — Juliet C Switzer
(74) *Attorney, Agent, or Firm* — Kening Li; Duane Morris LLP

(57) ABSTRACT

Differentially expressed miRNA or small mRNA in the culture media of embryos were found to correlate to and affect embryo developmental fate. Accordingly the present invention provides a method for selecting a bovine embryo for implantation into a female bovine animal for further development based on the levels of specific miRNA or small mRNA. Also provided are methods of improving bovine embryo development fate by reducing in the culture medium the level of selected miRNAs.

6 Claims, 4 Drawing Sheets
Specification includes a Sequence Listing.

(56) References Cited

OTHER PUBLICATIONS

Farh KKH, Grimson A, Jan C, Lewis BP, Johnston WK, Lim LP, Burge CB, Bartel DP: The widespread impact of mammalian microRNAs on mRNA repression and evolution. Science 2005, 310(5755):1817-1821.
Lim LP, Lau NC, Garrett-Engele P, Grimson A, Schelter JM, Castle J, Bartel DP, Linsley PS, Johnson JM: Microarray analysis shows that some microRNAs downregulate large numbers of target mRNAs. Nature 2005, 433(7027):769-773.
Bartel DP: MicroRNAs: Genomics, biogenesis, mechanism, and function. Cell 2004, 116(2):281-297.
Tang F, Kaneda M, O'Carroll D, Hajkova P, Barton SC, Sun YA, Lee C, Tarakhovsky A, Lao KQ, Surani MA: Maternal microRNAs are essential for mouse zygotic development. Genes & Development 2007, 21(6):644-648.
Tesfaye D, Worku D, Rings F, Phatsara C, Tholen E, Schellander K, Hoelker M: Identification and Expression Profiling of MicroRNAs During Bovine Oocyte Maturation Using Heterologous Approach. Molecular Reproduction and Development 2009, 76(7):665-677.
Hossain MM, Salilew-Wondim D, Schellander K, Tesfaye D: The role of microRNAs in mammalian oocytes and embryos. Animal Reproduction Science 2012, 134(1-2):36-44.
Mondou E, Dufort I, Gohin M, Fournier E, Sirard MA: Analysis of microRNAs and their precursors in bovine early embryonic development. Molecular Human Reproduction 2012, 18(9):425-434.
Kropp J, Salih SM, Khatib H: Expression of microRNAs in bovine and human pre-implantation embryo culture media. Front Genet 2014, 5:91.
Rosenbluth EM, Shelton DN, Wells LM, Sparks AET, Van Voorhis BJ: Human embryos secrete microRNAs into culture media-a potential biomarker for implantation. Fertility and Sterility 2014, 101(5):1493-1500.
Stenvang J, Petri A, Lindow M, Obad S. Kauppinen S: Inhibition of microRNA function by antimiR oligonucleotides. Silence 2012, 3(1):1.
Ebert MS, Neilson JR, Sharp PA: MicroRNA sponges: competitive inhibitors of small RNAs in mammalian cells. Nat Methods 2007, 4(9):721-726.
Parrish JJ, Krogenaes A, Suskoparrish JL: Effect of Bovine Sperm Separation by either Swim-Up Or Percoll Method on Success of In-Vitro Fertilization and Early Embryonic-Development Theriogenology 1995, 44(6):859-869.
Livak KJ, Schmittgen TD: Analysis of relative gene expression data using real-time quantitative PCR and the 2(T)(-Delta Delta C) method. Methods 2001, 25(4):402-408.
Huang W, Yandell BS, Khatib H: Transcriptomic profiling of bovine IVF embryos revealed candidate genes and pathways involved in early embryonic development RID B-5005-2011. Bmc Genomics 2010, 11:23-23.
Zhang B, Penagaricano F, Chen H, Khatib H: Novel transcripts and alternatively spliced genes are associated with early development in bovine embryos. Animal 2012, 6(8):1199-1205.
Driver AM, Huang W, Kropp J, Penagaricano F, Khatib H: Knockdown of CDKN1C (p57(kip2)) and PHLDA2 Results in Developmental Changes in Bovine Pre-implantation Embryos. Plos One 2013, 8(7):10.
Vandesompele J, De Preter K, Pattyn F, Poppe B, Van Roy N, De Paepe A, Speleman F: Accurate normalization of real-time quantitative RT-PCR data by geometric averaging of multiple internal control genes. Genome Biol 2002, 3(7): Research0034.
Xu B, Wang N, Wang XH, Tong N, Shao N, Tao J, Li PC, Niu XB, Feng NH, Zhang LH et al: MiR-146a suppresses tumor growth and progression by targeting EGFR pathway and in a p-ERK-dependent manner in castration-resistant prostate cancer. Prostate 2012, 72(11):1171-1178.
Guo SL, Peng Z, Yang X, Fan KJ, Ye H, Li ZH, Wang Y, Xu XL, Li J, Wang YL et al: miR-148a Promoted Cell Proliferation by Targeting p27 in Gastric Cancer Cells. International Journal of Biological Sciences 2011, 7(5):567-574.
Giglio S, Cirombella R, Amodeo R, Portaro L, Lavra L, Vecchione A: MicroRNA miR-24 promotes cell proliferation by targeting the CDKs inhibitors p27Kip1 and p16INK4a. Journal of Cellular Physiology 2013, 228(10):2015-2023.
Srivastava N, Manvati S, Srivastava A, Pal R, Kalaiarasan P, Chattopadhyay S, Gochhait S, Dua R, Bamezai RNK: miR-24-2 controls H2AFX expression regardless of gene copy number alteration and induces apoptosis by targeting antiapoptotic gene BCL-2: a potential for therapeutic intervention. Breast Cancer Research 2011, 13(2) : R39 eleven pages.
Xu Q, Jiang Y, Yin Y, Li Q, He J, Jing Y, Qi YT, Li W, Lu B, Peiper SS et al: A regulatory circuit of miR-148a/152 and DNMT1 in modulating cell transformation and tumor angiogenesis through IGF-IR and IRS1. Journal of Molecular Cell Biology 2013, 5(1):3-13.
Jeon YJ, Kim SY, Rah H, Choi DH, Cha SH, Yoon TK, Lee WS, Shim SH, Kim NK: Association of the miR-146aC > G, miR-149T > C, miR-196a2T > C, and miR-499A > G Polymorphisms with Risk of Spontaneously Aborted Fetuses. American Journal of Reproductive Immunology 2012, 68(5):408-417.
Mishra PJ, Song B, Wang Y, Humeniuk R, Banerjee D, Merlino G, Ju JF, Bertino JR: MiR-24 Tumor Suppressor Activity Is Regulated Independent of p53 and through a Target Site Polymorphism. Plos One 2009, 4(12): e8445 ten pages.
Lal A, Pan YF, Navarro F, Dykxhoorn DM, Moreau L, Meire E, Bentwich Z, Lieberman J, Chowdhury D: miR-24-mediated downregulation of H2AX suppresses DNA repair in terminally differentiated blood cells. Nature Structural & Molecular Biology 2009, 16(5):492-498.
Hassan MQ, Gordon JAR, Beloti MM, Croce CM, van Wijnen AJ, Stein JL, Stein GS, Lian JB: A network connecting Runx2, SATB2, and the miR-23a similar to 27a similar to 24-2 cluster regulates the osteoblast differentiation program. Proceedings of the National Academy of Sciences of the United States of America 2010, 107(46):19879-19884.
Sohel MMH, Hoelker M, Noferesti SS, Salilew-Wondim D, Tholen E, Looft C, Rings F, Uddin MJ, Spencer TE, Schellander K et al: Exosomal and Non-Exosomal Transport of Extra-Cellular microRNAs in Follicular Fluid: Implications for Bovine Oocyte Developmental Competence. Plos One 2013, 8(11) : e78505, sixteen pages.
Williams KC, Renthal NE, Condon JC, Gerard RD, Mendelson CR: MicroRNA-200a serves a key role in the decline of progesterone receptor function leading to term and preterm labor. Proceedings of the National Academy of Sciences of the United States of America 2012, 109(19):7529-7534.
Haraguchi H, Saito-Fujita T, Hirota Y, Egashira M, Matsumoto L, Matsuo M, Hiraoka T, Koga K, Yamauchi N, Fukayama M et al: MicroRNA-200a Locally Attenuates Progesterone Signaling in the Cervix, Preventing Embryo Implantation. Molecular Endocrinology 2014, 28(7):1108-1117.
Crosier AE, Farin PW, Dykstra MJ, Alexander JE, Farin CE: Ultrastructural morphometry of bovine blastocysts produced in vivo or in vitro. Biology of Reproduction 2001, 64(5):1375-1385.
Stowe HM, Curry E, Calcatera SM, Krisher RL, Paczkowski M, Pratt SL: Cloning and expression of porcine Dicer and the impact of developmental stage and culture conditions on MicroRNA expression in porcine embryos. Gene 2012, 501(2):198-205.

* cited by examiner

NON-INVASIVE ASSAYS FOR EMBRYO QUALITY

BACKGROUND OF THE INVENTION

The present invention relates to the identification of microRNAs and mRNAs in in vitro culture media as non-invasive biomarkers of embryo development, and to methods of improving the viability of in vitro cultured embryos.

Infertility has become a challenge in many mammalian species. In humans, about 15% of couples fail to conceive within the course of a year of unprotected sex. Within the United States, 10.9% of women aged 15-44 have impaired fecundity and about 6% are infertile [1]. A decline in fertility over the last 40-50 years has also been observed in dairy cattle. Conception rates in the 1950s were reported to be about 55% for artificially inseminated cows at observed estrus and by 1990 the rate declined to about 35% [2]. Selection intensity for higher milk production in dairy cattle has propagated a paralleled decline in fertility, posing a challenge to dairy producers [3]. Across species, a culmination of factors contributes to the decline in fertility including parental genetic contribution and environmental factors.

Assisted reproductive technologies (ARTS) have become well developed and utilized to overcome the challenges of infertility. These technologies are costly and rather inefficient, as a 2012 Fertility Clinics Success Rates Report demonstrated that of all fresh non-donor ART cycles started in 2012, only 36% resulted in pregnancy and of those 29% resulted in live birth [4]. Furthermore, the pregnancy rate of cows following transfer of in vitro produced embryos is only 45% and have increased risk for abortion and still birth compared to cows with in vivo produced embryos [5]. Conventionally, assessment of embryo quality and potential of in vitro produced embryos, in both humans and cattle, is largely based on morphology [6]. Morphologically similar embryos, however, differ in developmental capacity likely due to differences in the underlying genetics driving development [7]. Thus, there is need for better, non-invasive methods and biomarkers for efficient selection of embryos with enhanced developmental potential that will result in a live birth.

MicroRNA (miRNA) biomarkers have recently been identified for detection of several pathologies in humans. Indeed, Mitchell et al. [8] demonstrated that miRNAs secreted from prostate cancer cells into the blood could be detected in a patient's serum sample, offering a non-invasive method for diagnosing cancer. The presence of miRNAs in the extracellular environment has recently been reported in many bodily fluids including serum, saliva, urine, and placental fluid [8-14]. Studies have demonstrated the extreme stability of miRNAs in serum as they withstand freezing, thawing and pH changes [8, 11]. In the extracellular environment, miRNAs are predominantly bound to proteins such as Ago2 and NPM1 which provides stability, though a fraction is contained within exosomes [9, 10, 12]. Secretion of miRNAs into the extracellular environment is cell-specific, allowing for the development of biomarkers for a wide range of cell types and tissues.

MiRNAs play a role in nearly every cellular process including cell proliferation, differentiation, metabolism, apoptosis and cell signaling [15]. These small non-coding RNA molecules act in cells to regulate gene expression. Mature miRNAs are 18-22 nucleotides in length and are found predominantly in the cytoplasm where they are assembled into RNA-induced silencing complexes (RISC) [16]. Once assembled within a RISC, the guide strand of the miRNA hinds to the 3' UTR region of its target mRNA to either degrade or block translation of the mRNA, thereby blocking protein synthesis [16]. Imperfect binding to a miRNA's target mRNA allows for one miRNA to bind to a vast array of mRNA targets, increasing the regulatory potential of a single miRNA [17-19].

Embryonic development is partially driven by the underlying genetics of the embryo and as such miRNAs are dynamically expressed throughout the stages of development. In all cells, miRNA expression is precisely regulated in a developmental stage- and tissue-specific manner [18-20]. Similarly within gametes and embryos, the miRNA profile reflects differences in the competence and/or stage of development the cells are undergoing [21-24].

A study by Kropp et al. [25] provides evidence that miRNAs are differentially expressed between bovine blastocyst stage embryos and those which fail to develop, deemed degenerates. Therefore, miRNA expression in the gamete as well as the embryo is of great importance and dysregulation of key miRNAs could consequently alter development of the embryo.

Kropp et al. also reported the presence of miRNAs in bovine and human IVF culture media [25]. Similarly, Rosenbluth et al. [26] detected miRNAs in human IVF culture media and differential miRNA expression was correlated to pregnancy outcome and chromosomally abnormal embryos. These studies are limited in the number of miRNAs detected as they used only a few candidate miRNAs [22] or utilized a heterologous array for detection of miRNA [23]. Prior to the present invention, there has never been any report that the miRNA levels in the culture medium also were different among embryos of different developmental fate and can be used as indicators of embryo viability.

Likewise, mRNAs are packaged into exosomes and are secreted by cells into the extracellular environment (Valadi et al., 2007). However, there has been no report that specific mRNAs present in culture medium can be used as biomarkers for predicting embryo developmental prospect.

Furthermore, there has not been any report that supplementing or depleting specific miRNAs in the culture media can improve the developmental fate of an embryo.

SUMMARY OF THE INVENTION

The present invention relates to the use of 11 microRNAs (miRNA) and 18 mRNAs as indicators of healthy IVF embryo development.

In one aspect, the inventors used small-RNA sequencing technology and identified both known and novel miRNAs in culture media of embryos of varying competence, and found that identification of differentially expressed miRNAs could be used as molecular markers of embryo quality.

In addition, the present inventors showed that similar to other cell types, embryos also secrete mRNAs to culture media, which provides an additional means to non-invasively survey the embryo for its developmental potential. Media derived from embryos of differing competence or quality was deep-sequenced to identify mRNAs present. Many small mRNA fragments were identified in the media between two groups of embryos varying in developmental ability. These molecules were found to provide the framework for testing in morphologically similar embryos to assess embryo development and fertility in cattle to improve reproductive efficiency.

Small-RNA sequencing revealed 11 differentially expressed miRNAs (SEQ ID NOs: 1-11) in IVF culture media conditioned by either blastocysts or degenerate embryos. By comparing the miRNAs in culture media from healthy embryos and those from degenerate embryos in three different IVF experiments, it is found that high expression levels of 11 specific miRNAs in the culture media correlated with degenerate embryo development. Among the miRNAs sequences, some are known to be present in cows, some known to be present in other animals and a few are novel bovine sequences.

To better understand the interplay of miRNA expression between the extracellular environment, miR-24, a highly conserved and differentially expressed miRNA in the media, was further examined for functional analysis. Addition of a mimic of miR-24 to the media of day-5 embryos decreased embryonic development and repressed its target gene. These data suggest that miRNAs in the media are not only secreted, but also are taken up by the embryo and affect gene expression driving embryonic development.

Similarly, 19 mRNAs (SEQ ID NOs: 12-29) have been found to be differentially expressed in the culture medium between blastocysts and degenerate embryos.

Accordingly, in one embodiment, the present invention provides a method for selecting a bovine embryo cultured in a culture medium suitable for implantation into a female bovine animal for further development, the method comprising a) extracting RNA from the culture medium; b) detecting an expression level of an miRNA selected from the group consisting of bta-mir-2887, bta-miR-24-3p, ssc-miR-22, PC-3p-21760, ssc-miR-423-5p, bta-miR146a, bta-miR-191, bta-mir-2904, bta-miR-186, bta-miR-148a, and bta-miR-192 (SEQ ID NOs:1-11) or an mRNA selected from the group consisting of SEQ ID NOs: 12-29; c) transferring the embryo into a female bovine for further development if the expression level of an miRNA selected from the group consisting of SEQ ID NOs: 1-11 is decreased; or if the expression level of one of a small mRNA comprising a sequence selected from the group consisting of SEQ ID NOs: 12-29 is increased.

In another embodiment, the miRNA is selected from a group consisting of miR-2887, miR-24, miR-191, and miR-148a.

In another embodiment, the miRNA or mRNA is converted to DNA via reverse transcription and the DNA is further amplified via a polymerase chain reaction.

In one embodiment, an embryo is selected and implanted into a suitable female animal if the expression level of bta-miR-24-3p is decreased in the culture medium.

In one embodiment, an embryo is selected and implanted if the expression level of a small mRNA comprising the nucleotide sequence of SEQ ID NO: 12 or SEQ ID NO: 14 is increased.

In one embodiment, an embryo has been grown in the culture media in vitro for at least about 3 days before a selection is made. In another embodiment, the embryo has developed into a blastocyst. In one embodiment, the embryo is formed from an oocyte that was fertilized by in vitro fertilization. In another embodiment, the in vitro fertilization includes gamete co-culture. In another embodiment, fertilization is carried out via intracytoplasmic sperm injection (ICSI).

In one embodiment, the present invention provides a method for improving viability of an embryo grown in a culture medium in vitro, the method comprising reducing in the culture medium the level of an miRNA selected from the group consisting of bta-mir-2887, bta-miR-24-3p, ssc-miR-22, PC-3p-21760, ssc-miR-423-5p, bta-miR146a, bta-miR-191, bta-mir-2904, bta-miR-186, bta-miR-148a, and bta-miR-192 (SEQ ID NOs:1-11).

In one embodiment, the embryo is cultured in a medium to which an miRNA inhibitor specific for the miRNA listed above (i.e. SEQ ID NO: 1-11) has been added. The miRNA inhibitor may be double-stranded RNAs, short interfering RNAs (siRNA), antisense nucleic acids, anti-miRNA oligo-nucleotides (AMOs), molecules of enzymatic RNA, or ribozymes.

The present invention further provides a kit comprising a reagents for detecting each of SEQ ID NO: 1-29, which may further comprise one or more enzymes for performing any step of RT-PCR, and or a suitable label.

DESCRIPTION OF THE INVENTION

Figure 1:
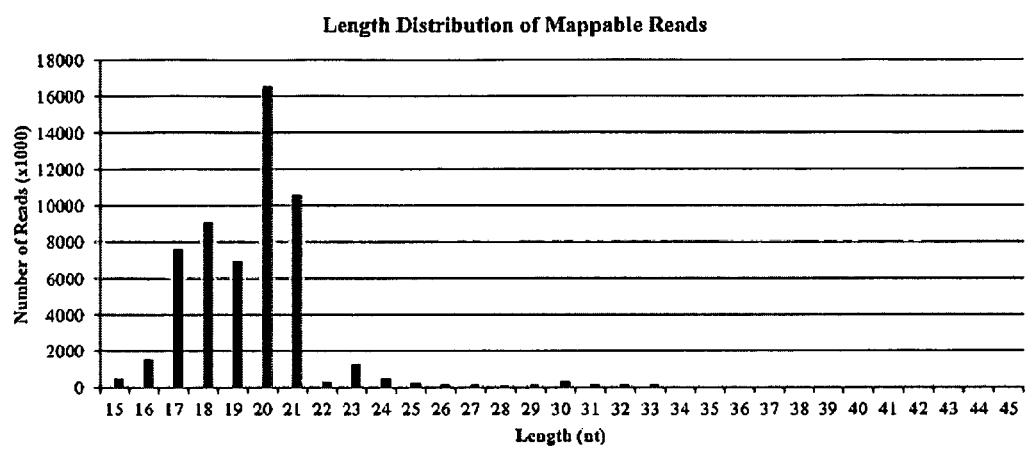
FIG. 1 shows the length distribution of mappable miRNA reads.

Herein it is disclosed that the presence of miRNA in the culture media of IVF produced embryos can be used as biomarkers of embryo quality.

The present inventors have also identified a total of 18 mRNAs differentially expressed, consistently across multiple IVF replicates, between blastocyst and degenerate media.

In one embodiment, the present invention provides a method for determining whether an embryo in an artificial culture medium is suitable for implantation into a female (bovine) animal for further development, the method comprising a) extracting RNA from the culture medium; b) detecting an expression level of an miRNA selected from the group consisting of bta-mir-2887, bta-miR-24-3p, ssc-miR-22, PC-3p-21760, ssc-miR-423-5p, bta-miR146a, bta-miR-191, bta-mir-2904, bta-miR-186, bta-miR-148a, and bta-miR-192 (SEQ ID NOs:1-11) or an mRNA selected from the group consisting of SEQ ID NOs: 12-29; 3) transferring the embryo into a female bovine for further development if the expression level of an miRNA selected from the group consisting of SEQ ID NOs: 1-11 is decreased; or if the expression level of one of a small mRNA comprising a sequence selected from the group consisting of SEQ ID NOs: 12-29 is increased. In one embodiment, the miRNA is selected from a group consisting of miR-2887, miR-24, miR-191, and miR-148a. In another embodiment, the miRNA or mRNA is converted to DNA via reverse transcription and the DNA is further amplified via a polymerase chain reaction. In one embodiment, an embryo is selected and transferred if the expression level of bta-miR-24-3p is decreased in the culture medium. In one embodiment, an embryo is selected and transferred if the expression level of a small mRNA comprising the nucleotide sequence of SEQ ID NO: 12 or SEQ ID NO: 14 is decreased. In one embodiment, an embryo has been grown in the culture media in vitro for at least about 3 days before a selection is made. In another embodiment, the embryo has developed into a blastocyst. In one embodiment, the embryo is formed from an oocyte that was fertilized by in vitro fertilization. In another embodiment, the in vitro fertilization includes intracytoplasmic sperm injection (ICSI).

Various established and well-known methods are available in the art for determining whether the expression level of an miR or an mRNA is decreased or increased, taking into account of the differences in cellular input, variations in cultural conditions of the embryos, technical issues such as the quality of the RNA isolated, and the efficiency of the techniques (e.g. reverse transcription reaction). See e.g. Analysing Gene Expression, A Handbook of Methods: Possibilities and Pitfuls. Lorkowski and Cullen (eds), John Wiley and Sons, (2006). For example, an invariably expressed internal control gene such as a housekeeping gene can be used, an average standard can be established using a large number of samples, and a standard curve can be established using an external standard.

As used herein, the term "MicroRNA" means an endogenous non-coding RNA between 18 and 25 nucleobases in length, which is the product of cleavage of a pre-miRNA by the enzyme Dicer. Examples of mature miRNAs are found in the miRNA database known as miRBase. In certain embodiments, microRNA is abbreviated as "miRNA" or "miR."

"Pre-miRNA" or "pre-miR" means a non-coding RNA having a hairpin structure. The nuclear RNasc III Drosha cleaves primary miRNAs (pri-miRNAs) to release hairpin-shaped pre-miRNAs that are subsequently cut by the cytoplasmic RNase III Dicer to generate mature miRNAs.

"Stem-loop sequence" means an RNA having a hairpin structure and containing a mature miRNA sequence. Pre-miRNA sequences and stem-loop sequences may overlap. Examples of stem-loop sequences are found in the miRNA database known as miRBase.

"Pri-miRNA" or "pri-miR" means a non-coding RNA having a hairpin structure that is a substrate for the double-stranded RNA-specific ribonuclease Drosha.

"miRNA precursor" means a transcript that originates from a genomic DNA and that comprises a non-coding, structured RNA comprising one or more miRNA sequences. For example, in certain embodiments a miRNA precursor is a pre-miRNA. In certain embodiments, a miRNA precursor is a pri-miRNA.

The presently disclosed methods may include detecting expression of miRNA or mRNA. "Expression" means any functions and steps by which a gene's coded information is converted into structures present and operating in a cell. Detecting expression of miRNA or mRNA may include detecting nucleic acid comprising mRNA, miRNA, pre-miRNA, or pri-miRNA by suitable methods known in the art, including methods that include one or more of the following: reverse transcription, polymerase chain reaction, probing, targeting, and hybridization. MicroRNA expression may be assessed via detecting nucleic acid comprising miRNA, pre-miRNA, or pri-miRNA in an extracellular sample (e.g., in culture media in which an embryo has been grown) or in an intracellular sample (e.g., an intracellular sample of an embryo).

Detection methods may include hybridizing an oligonucleotide reagent such as a primer or a probe to the miRNA and detecting hybridization of the primer or probe to the mRNA or miRNA. Suitable oligonucleotide reagents may include RNA probes and DNA probes, which optionally include a label (e.g., a radioisotope label, an enzymatic label, a fluorophore label, and the like).

Detection methods may include converting the mRNA or miRNA to DNA via performing reverse transcription and amplifying the DNA via performing a polymerase chain reaction (RT-PCR). RNA linkers may be ligated to the miRNA prior to converting the miRNA to DNA and/or DNA linkers may be ligated to the DNA prior to amplifying the DNA. Multiple miRNAs may be detected in the methods (e.g., at least 2, 3, 4, 5, 6, 7, 8, 9, 10, 11, 12, 13, 14, 15, 16, 17, 18, 19, or 20 miRNAs) and microarrays comprising probes for multiple miRNAs may be utilized to detect multiple miRNAs.

As used herein, the term "detecting expression of an mRNA or miRNA" means determining that the mRNA or miRNA is being expressed or not, and if yes, the level of expression. In some embodiments, expression may be detected relative to expression of a control nucleic acid.

Methods and kits of the present invention may utilize or include oligonucleotide reagents for detecting miRNAs. As contemplated herein, "oligonucleotide reagents" may include oligonucleotides that hybridize specifically to a selected mRNA or miRNA and that may be used to detect the mRNA or miRNA based on the specific hybridization. For example, the oligonucleotide reagents may include one or more primers for performing any or all steps of RT-PCR performed on mRNA or miRNA as contemplated herein (i.e., a primer for performing reverse transcription (RT) of an mRNA or miRNA to obtain reverse transcribed miRNA and/or one or a pair of primers for performing polymerase chain reaction (PCR) of the reverse transcribed miRNA to obtain an amplified product). The reverse transcribed mRNA or miRNA or amplified product then may be detected by methods known in the art. Oligonucleotide reagents may include probes for detecting an mRNA or miRNA and/or any product of RT-PCR performed on miRNA (e.g., a probe for detecting a reverse transcribed mRNA or miRNA, or a probe for detecting an amplified product of the reverse transcribed miRNA). Primers and probes as contemplated herein may include a label.

The disclosed methods may be utilized to detect expression of one or more mRNA or miRNAs by an embryo or the lack of expression of one or more mRNA or miRNAs by an embryo, for example in order to assess embryo viability, or its development prospect. The disclosed methods also may be utilized to optimize culture media for an embryo via adding one or more miRNAs to the culture media or depleting one or more miRNAs from the culture media.

As used herein, the term "subject" or "individual" may encompass a human patient. The disclosed methods may include selecting an embryo for implantation based on detecting expression of one or more miRNAs, and subsequently implanting the embryo in a subject. As such, the term "patient" is meant to encompass a person that has elected to undergo implantation of an embryo into the patient's uterus. In some embodiments, the methods may include requesting a test that provides the results of an analysis of expression of one or more miRNAs in a sample obtained from an embryo grown in vitro (e.g., an intracellular sample or an extracellular sample such as culture media in which the embryo has been grown); selecting an embryo for implantation in a subject based on the results of the test; and optionally, implanting the selected embryo in a patient's uterus. The embryo utilized in the disclosed methods may be an embryo obtained by in vitro fertilization (IVT) procedure, for example, by intracytoplasmic sperm injection (ISCI)). In one embodiment, a modification of the multiple ovulation and embryo transfer (MOET) procedure can be used, especially for bovine. Specifically, females are superovulated, eggs are collected, in vitro fertilized, e.g. using semen from superior males and implanted into other females allowing for use of the superior genetics of the female (as well as the male) without having to wait for her to give birth to one calf at a time. Developing blastomeres at the 4-8 cell stage may be cultured in vitro and then assayed for their developmental prospect, and selection decisions for re-implantation made accordingly.

In another embodiment, the present invention provides a method for improving viability of an embryo grown in a culture medium in vitro, the method comprising reducing in the culture medium the level of an miRNA selected from the group consisting of bta-mir-2887, bta-miR-24-3p, ssc-miR-22, PC-3p-21760, ssc-miR-423-5p, bta-miR146a, bta-miR-191, bta-mir-2904, bta-miR-186, bta-miR-148a, and bta-miR-192 (SEQ ID NOs:1-11); or increasing in the culture medium the level of a small mRNA comprising a sequence selected from the group consisting of SEQ ID NOs: 12-29.

In one embodiment, the embryo is cultured in a medium to which an miRNA inhibitor specific for the miRNA listed above (i.e. SEQ ID NO: 1-11) has been added. The miRNA inhibitor may be double-stranded RNAs, short interfering RNAs (siRNA), antisense nucleic acids, anti-miRNA oligonucleotides (AMOs), molecules of enzymatic RNA, or ribozymes.

Suitably, the miR inhibitor is capable of specifically inhibiting (silencing) the activity of a target miRNA or preventing the binding of the miRNA to the specific binding sites in its target RNAs. An miRNA inhibitor can comprise double-stranded RNA, short interfering RNA (siRNA), antisense nucleic acids, anti-miRNA oligonucleotides (AMOs), molecules of enzymatic RNA, or ribozymes. Another approach for miRNA inhibition is the so-called miRNA sponges.

An AMO sequesters its corresponding mature miRNA in competition with cellular target mRNA leading to functional inhibition of the miRNA and de-repression of the target mRNA. AMOs are described in detail in Stenvang et al. 2012, Silence 3:1-17, incorporated herein by reference in its entirety. The oligonucleotides include both naturally occurring nucleotides, and non-naturally occurring nucleotide analogues.

Preferably, the analogues have a functional effect on the way in which the oligomer works to bind to its target; for example by producing increased binding affinity to the target and/or increased resistance to nucleases and/or increased ease of transport into the cell. Incorporation of affinity-enhancing analogues in the oligomer, including Locked Nucleic Acid (LNA), can allow the size of the specifically binding oligomer to be reduced and may also reduce the upper limit to the size of the oligomer before non-specific or aberrant binding takes place. Modifications to the nucleotides include modified sugar or base moieties, such as bicyclic nucleotides or 2' modified nucleotides. In some embodiments, the chemical modification is one or more of a 2'-O-alkyl-RNA unit, 2'-OMe-RNA unit, 2'-amino-DNA unit, 2'-fluoro-DNA unit (including, but not limited to, a DNA analogue with a substitution to a fluorine at the 2' position (2'-F), Locked Nucleic Acid (LNA) unit, peptide nucleic acid (PNA) unit, anhydrohexitol nucleic acids (HNA) unit, intercalating nucleic acid (INA) unit, and a 2' MOE RNA unit.

In various embodiments, the inhibitor comprises an antisense oligonucleotide comprising 16 or fewer nucleotides or is about 7 to about 8 nucleotides, and a sequence that is at least partially complementary to a mature sequence of an miR listed above. The antisense oligonucleotide comprises a sequence that is at least partially complementary to a mature sequence of the target miR, and optionally one or more chemically modified nucleotides as described above.

miRNA sponges are plasmid constructs either transiently or stably transfected into mammalian cells containing multiple miR-binding sites for a chosen miRNA gene (see e.g. MicroRNA sponges: competitive inhibitors of small RNAs in mammalian cells, Ebert et al., Nature Methods, 2007, 4:721-726).

Many miRNA inhibitors are commercially available, e.g. the miScript miRNA Inhibitors from Qiagen®, which are chemically synthesized, single-stranded, modified RNAs which specifically inhibit endogenous miRNA function after transfection or unassisted uptake into cells; and the mirVana™ miRNA Inhibitors from Life Technologies, which are small, chemically modified, single-stranded RNA molecules designed to specifically bind to and inhibit endogenous miRNA molecules by down-regulation of miRNA activity.

miRNA mimics (miR-mimics) that enhance or mimic endogenous miRNA functions are also readily available to those ordinarily skilled in the art, and are widely used for gene silencing. miR-mimics commonly include non-natural double-stranded miRNA-like RNA fragments. Such an RNA fragment is designed to have its 5'-end bearing a partially complementary motif to the selected sequence in the 3'-UTR unique to the target gene. Once introduced into cells, this RNA fragment, mimicking an endogenous miRNA, can bind specifically to its target gene and produce posttranscriptional repression, more specifically translational inhibition, of the gene. Unlike endogenous miRNAs, miR-Mimics act in a gene-specific fashion. The miR-Mimic approach belongs to the "miRNA-targeting" and "miRNA-gain-of-function" strategy and is primarily used as an exogenous tool to study gene function by targeting mRNA through miRNA-like actions in mammalian cells (see e.g. Xiao, et al. J Cell Physiol 212:285-292, 2007; Xiao et al. Nat Cell Biol, in review).

miR-mimics are also commercially available, e.g. the miScript miRNA Mimics from Qiagen®, which are chemically synthesized, double-stranded RNAs which mimic mature endogenous miRNAs after transfection or unassisted uptake into cells; the Exiqon® microRNA Mimics sold under the trade name miRCURY LNA™ microRNA Mimics, which has a triple RNA strand design; and the MISSION miRNA mimics from Sigma-Aldrich®, which are small, double-stranded RNA molecules.

Both miRNA inhibitors and miR-mimics can enter the target cell or tissue via transfection or unassisted uptake by the cells or embryos itself, the latter maybe more preferred due to minimal adverse effect on the developing embryos.

The present invention further provides a kit comprising reagents for detecting each of SEQ ID NO: 1-29, such as suitable primers or probes specific for the detection of the above sequences, one or more enzymes for performing any step of RT-PCR, and or a suitable label. As used herein, the term "kit" refers to a system for delivering materials, such as systems for the storage, transport, or delivery of reaction reagents (e.g., oligonucleotides, enzymes, etc. in appropriate containers) and/or supporting materials (e.g., buffers, written instructions for performing the assay etc.) from one location to another. For example, kits include one or more enclosures (e.g., boxes) containing the relevant reaction reagents and/or supporting materials. The term "kit" includes both fragmented and combined kits. The term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides. A "combined kit" refers to a delivery system containing all of the components of a reaction assay in a single container (e.g., in a single box housing each of the desired components). In some embodiments, the present invention provides reagent kits comprising one or more of the components necessary for practicing the present invention. The kit may include any and all components necessary or desired for assays including, but not limited to, the reagents themselves, buffers, control reagents (e.g., tissue samples, positive and negative control target oligonucleotides, etc.), solid supports, labels, written and/or pictorial instructions and product information, software (e.g., for collecting and analyzing data), inhibitors, labeling and/or detection reagents, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered The invention is illustrated by the following examples, which are not intended to be limiting in any way. Also. all references cited herein are incorporated by reference in their entirety.

EXAMPLES

Example 1

Materials and Methods
In Vitro Production of Embryos

As previously described in the study of Kropp et al. [25], which is specifically incorporated herein by reference, 3 replicates of embryos and culture media were procured utilizing an IVF system. In brief, ovaries were obtained from a local slaughter house and follicles of 2-10 mm were aspirated. Oocytes were washed twice in Tyrode's albumin lactate pyruvate (TALP)-Hepes buffer and incubated in a cohort of 10 oocytes per 50 μL drop of M-199 media for 20 hours for maturation. Oocytes were then washed in TALP-Hepes buffer and transferred to 44 μL drops of IVF-TL media (Millipore, Phillipsburg, N.J.) supplemented with fatty-acid-free bovine serum albumin (FAF-BSA), sodium pyruvate and gentamicin. Sperm were prepared using the swim-up protocol as described by Parrish et al. [27] where the final concentration was adjusted to 1 million sperm/ml. Oocytes were co-incubated with sperm for 24 hours; deemed day 0.

After 24 hours, presumptive zygotes were stripped of their cumulus cells and washed in TALP-Hepes buffer. The presumptive zygotes were then placed in cohorts of 25 per 50 μL drops of synthetic oviductal fluid (SOF) media (Millipore) supplemented with FAF-BSA, sodium pyruvate and gentamicin to be cultured until day 5. On day 5, embryos were morphologically assessed and those which showed characteristics of a compacted morula were transferred to a fresh 50 μL drop of SOF media lacking BSA supplementation and cultured individually.

On day 8, embryos were morphologically assessed and deemed either a blastocyst or degenerate and pooled together; respectively. In parallel, the media conditioned by a single blastocyst or degenerate embryo was collected and respectively pooled together. Additionally, control SOF media (lacking BSA supplementation) was collected which was cultured within the same plate as the embryo but was not conditioned by a growing embryo. Three replicates were generated for sequencing utilizing a separate sire for each pool (see Table 1 for pool design).

TABLE 1

IVF Development Data and Pool Design.
Replicates: 1-3 miRNA-sequenced pools; 4-5 qRT-PC validation pools

| Replicate | Bull ID | Total Oocytes | Fertilization Rate (%) | Blastocyst Rate (%) | Media drops (n) per pool B/D* |
|---|---|---|---|---|---|
| 1 | A | 574 | 72.23 | 22.65 | 31 |
|   |   |   |   |   | 25 |
| 2 | B | 398 | 77.64 | 10.03 | 11 |
|   |   |   |   |   | 25 |
| 3 | C | 647 | 72.02 | 13.30 | 27 |
|   |   |   |   |   | 63 |
| 4 | B | 426 | 72.63 | 13.48 | 30 |
|   |   |   |   |   | 48 |
| 5 | C | 411 | 69.25 | 8.93 | 15 |
|   |   |   |   |   | 53 |

B/D* B: blastocyst media D: degenerate media

MiRNA Extraction from Culture Media

Extraction of miRNA from culture media samples was carried out using a cell free specific kit, the miRNeasy Serum/Plasma kit (Qiagen, Germantown, Md.). The input volume for extraction was 200 μL for each sample. To meet small-RNA sequencing input requirements, multiple extractions of each sample were carried out where the eluted miRNA samples from each extraction were pooled together. RNA was quantified using NanoDrop ND-1000 spectrophotometer (NanoDrop Technologies, Wilmington, Del.) and sequenced (LC Sciences, Houston, Tex.).

Small RNA Library Construction and Deep Sequencing

Small-RNA library preparation was carried out by LC Sciences using the Illumina TruSeq™ Small-RNA Preparation kit following the manufacturer's guidelines. The library generated was then clustered on Illumina's Cluster Station followed by sequencing on an Illumina GAIN instrument.

RNA-Sequencing Data Analysis

Sequencing data was analyzed using the LC Sciences proprietary pipeline. The raw sequenced reads were extracted, filtered and those which were between 15 and 32 bases in length were clustered into families deemed unique sequences (family of raw sequencing reads with the same sequence).

Figure 5:
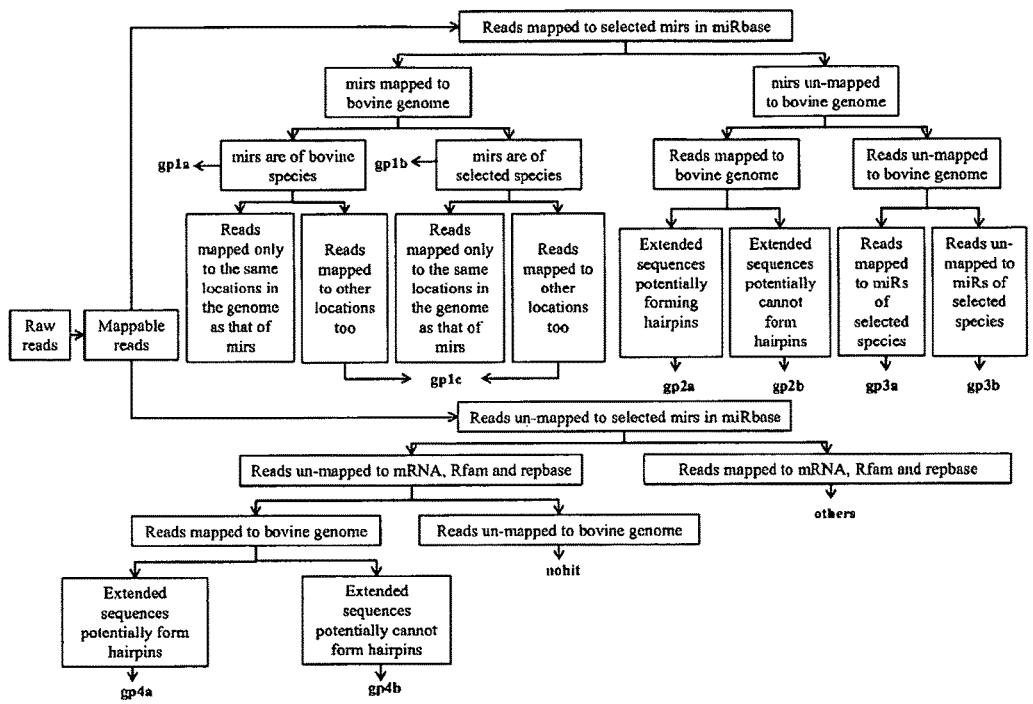
FIG. 5 shows the Sequencing Data Analysis of Mappable Reads (gp: group)

Unique sequences were mapped to pre-miRNA (denoted as mir) and mature miRNA (denoted as miR) sequences listed in miRbase of bovine or comparatively to other selected mammalian species; see FIG. 5. Mappable sequences were divided into 2 groups those that were mapped to selected mirs and mapped to species specific genome (group 1) or those that were not mapped to the species specific genome (group 2 and group 3). Group 1 was split into 3 sub-groups. Group 1a was those that were mapped to selected miRs in miRbase, were mapped to the bovine genome and are known miRs of the bovine species. Group 1b sequences mapped to selected miRs in miRbase, were mapped to the bovine genome and arc known miRs in other selected mammalian species. Group 1c includes sequences which mapped not only to the location of known miRs but also to other loci within the bovine genome. Group 2 miRs include both group 2a and 2b sequences that mapped to miRs of selected species, but not mapped to the bovine genome. Group 2a included those that the extended sequences at that position could potentially form hairpins whereas group 2b the extended sequences at the mapped position could not form hairpins. Group 3a miRs were those unique sequences mapped to miRs of selected species, but the miRs did not map to the bovine genome, however, sequences were mapped to selected mammalian species. Criteria was similar for group 3b in that miRs did not map to the bovine genome, however, though the miRs mapped to mirs in miRbase they did not map to the selected mammalian species chosen for analysis. Those that were unmapped to selected miRs in miRbase were further divided into 2 subgroups: group 4a and group 4b where both groups did not map to selected miRs of bovine but did map to the genome. Group 4a sequences were in a location where the extended sequence were likely to form a hairpin, whereas group 4b extended sequences were not likely to form hairpins. The program UNAFold (The RNA Institute, University at Albany, N.Y.) was used to calculate the secondary structure such as the likelihood to form hairpins from the precursor sequence.

Sample Comparison and Statistical Analysis of Sequencing Data

From each sample the total number of reads was tracked and normalized by dividing the number of reads by a library size parameter of the corresponding sample. The library size parameter is a median value of the ratio between the counts of a specific sample and a pseudo-reference sample. A count number in the pseudo-reference sample is the count geometric mean across all samples $$S_j = I_i\left(\frac{\sigma_{ij}}{(\prod_{k=1}^{m} \sigma_{ik})^{1/m}}\right)$$

where, $S_j$ is the library size parameter; $c_{ij}$ is the count number of sequence i sample j; m is the total number of samples involved. A paired t-test was carried out across the data from samples of the 3 replicates (1-3; Table 2) where significance was set at p<0.05.

TABLE 2

MiR-24 mimic reduces development

| Treatment Group | Total | Blastocysts | Degenerates | % Morula Developed to Blastocyst |
|---|---|---|---|---|
| Control | 156 | 118 | 38 | 75.6%[a] |
| 1 µM Mimic | 149 | 72 | 77 | 48.3%[b] |

Differing superscripts within a column denote statistically significant differences (p < 0.001).

Real-Time Quantitative PCR (qRT-PCR) for miRNA Gene Expression Validation

Of the significant miRNAs found to be differentially expressed, 5 were chosen to be validated technically by qRT-PCR and biologically in 2 additional replicates. Extracted miRNA for each sample was reverse transcribed into cDNA by the Miscript II RT kit (Qiagen). The HiSpec buffer was used per kit recommendation for subsequent quantification of mature miRNA. qRT-PCR to assess gene expression between samples was carried out using the miScript SYBR Green Kit (Qiagen). For each miRNA, a specific primer for its mature sequence was designed and obtained from Qiagen; see Table 3. The qRT-PCR reactions were carried out in a Bio-Rad iCycler real-time PCR machine with the following cycling conditions: 95° C. for 15 minutes followed by 40 cycles of 94° C. for 15 s, 55° C. for 30 s, and 70° C. for 30 s. The threshold for detection was set as a Ct<34. Data was then analyzed using the $2^{-\Delta\Delta Ct}$ method by Livak and Schmittgen [28].

TABLE 3

Quantitative Real-time PCR Primer Sequences

| Gene | Primer Sequence (5'-3') |
|---|---|
| miR-2887-2-3p | GGUGCGGAGAGCCCUUCGUCCCGGGA (SEQ ID No.: 30) |
| miR-24-3p | UGGCUCAGUUCAGCAGGAACAG (SEQ ID No.: 31) |
| miR-146a | UGAGAACUGAAUUCCAUAGGUUGU (SEQ ID No.: 32) |
| miR-191 | CAACGGAAUCCCAAAAGCAGCUG (SEQ ID No.: 33) |
| miR-148a | UCAGUGCACUACAGAACUUUGU (SEQ ID No.: 34) |
| miR-39* | UCACCGGGUGUAAAUCAGCUUG (SEQ ID No.: 35) |
| CDKN1b | F: CCCAGAGGACACGCATTTGG (SEQ ID No.: 36) R: AGGAGAGGAATCATCTGCGGC (SEQ ID No.: 37) |
| GAPDH | F: TGCCCAGAATATCATCCC (SEQ ID No.: 38) R: AGGTCAGATCCACAACAG (SEQ ID No.: 39) |

*C. elegans miR-39 Spike-in Control

MiRNA Mimic Supplementation to Embryos

IVF embryos were procured as aforementioned, however, on day 5 a cohort of 5-10 morula were transferred to a fresh drop of SOF media lacking BSA supplementation. A miRNA mimic of miR-24 was obtained from Qiagen. The concentration recommended by Qiagen for cell culture was scaled down based on the relative cell number and volume of media in our IVF culture system. The miRNA mimic was reconstituted in water and was added to the media at a final concentration of 1 µM. Additionally, morula were transferred to drop where nuclease-free water (vehicle of mimic) was added at the same volume as the mimic and cultured as control embryos. On day 8, embryos were morphologically assessed and the number of blastocyst and degenerate embryos in each experimental group (mimic or control) was counted. Embryo development was calculated as the percentage of morula that reached the blastocyst stage. Blastocyst and degenerate embryos were collected for each experimental group.

Gene Expression Analysis of miR-24 and mRNA Targets in Embryos

To assess miR-24 expression in mimic supplemented and control embryos, an Ambion RNAqueous-Micro Total RNA Isolation kit (Life Technologies, Austin, Tex.) was used to isolate total RNA from embryos following the kit recommendation to add 1.25 volumes of ethanol to capture small RNA. Then total RNA was reverse transcribed using the Miscript II RT kit (Qiagen). The HiFlex buffer was used for subsequent quantification of both mature miRNA and mRNA. Each cDNA reaction was diluted with water at a ratio of 1:5 and combined with 2× Quantitect SYBR green (Qiagen), water and either a universal primer and miR-24 primer assay or the primer for the housekeeping gene, glyceraldehyde 3-phosphate dehydrogenase (GAPDH). The GAPDH gene was chosen as an internal control because, in our previous studies of embryo samples (Huang et al., 2010; Zhang et al., 2012; Driver et al., 2013), its expression was the most stable in comparison to RPLP0 (ribosomal protein, large, P0) and ACTB (actin, beta) using the Vandesompele method (Vandesompele et al., 2002). Primer sequences are listed in Table 3. The qRT-PCR reactions were carried out in a BioRad iCycler with the following conditions: 95° C. for 15 minutes, followed by 40 cycles of 94° C. for 15 s, 55° C. for 30 s, and 70° C. for 30 s.

Additionally, embryos were tested for expression of a miR-24 target mRNA, cyclin-dependent kinase inhibitor 1b (CDKN1b). For gene expression analysis, the extracted RNA from embryos described above was reverse transcribed using the iScript cDNA synthesis kit (Bio-Rad Laboratories, CA). Real-time PCR reactions were carried out using the iQSYBR Green Supermix kit (Bio-Rad Laboratories, CA). Primers for qRT-PCR were designed to span exon-exon junctions to minimize amplification of genomic DNA and their sequences can be found in Table 3. The housekeeping gene GAPDH was used as an internal control in these reactions.

Statistical Analysis of Gene Expression

Analysis of gene expression data and graph generation was completed using the software OriginLab. For gene expression validation of selected miRNAs, a t-test was used to assess differences of the mean ΔCt between degenerate and blastocyst conditioned media for each miRNA. A one-way ANOVA, with Fisher's LSD, comparing the mean ΔCt of miR-24 expression across the stages of development was completed. A paired t-test was used to assess expression differences within embryos cultured with or without mimic. For each analysis the p-value was set as p<0.05.

Results

Analysis of Raw Small RNA Sequencing Data

Figure 6:
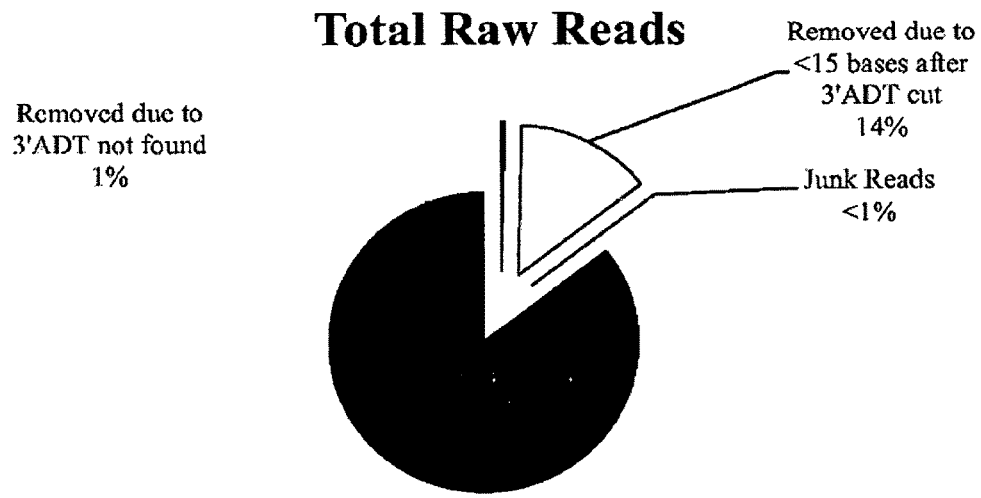
FIG. 6 shows the distribution of raw sequencing reads

To assess the milieu of miRNA in in vitro culture media from embryos of differing quality, conditioned media was collected from both blastocyst and degenerate (an embryo which failed to develop from the morula to blastocyst stage) embryos for small RNA sequencing. The media of the embryos in addition to the baseline control SOF (Synthetic Oviductal Fluid) media which did not contain an embryo was pooled and small RNA was extracted before sequencing. A total of 68,948,165 raw reads were obtained from RNA sequencing across all media samples. After filtering for reads that did not contain a 3' adapter (3'ADT) and those that were less than 15 bases after 3'ADT removal, a total of 58,870,746 reads were obtained and analyzed using the proprietary pipeline by LC Sciences (Houston, Tex.); see FIG. 6. Analysis of the length distribution showed that reads were of expected length of 17-22 nucleotides, where the greatest percentage (28%) of mappable reads were 20 nucleotides in length (FIG. 1). Reads were either mapped to selected mirs (pre-mature miRNA) and miRs (mature miRNA) in miRbase of both bovine and selected mammalian species, or were un-mapped to selected mirs in miRbase of both bovine and selected mammalian species (Table 4). Using the program UNAFold, reads that were not mapped to known miR or mirs were further categorized based on the likelihood to form a hairpin and/or whether the sequence mapped to the bovine genome including other areas such as mRNA and other RNAs (Table 4). Sequences were considered a "nohit" if they did not map to either miRbase, RepBase, or to the bovine reference genome.

TABLE 4

Classification of Sequenced Reads

| | # Seqseq |
|---|---|
| Raw | 68,948,165 |
| Total mappable | 58,870746 |
| Group 1a | 15,028 |
| Group 1b | 3,302 |
| Group 2a | 331 |
| Group 2b | 942 |
| Group 3a | 2,952 |
| Group 3b | 68 |
| Group 4a | 22,336 |
| Group 4b | 8,805,573 |
| Mapped to mRNA | 9,128,304 |
| Mapped to other mRNA | 940,719 |
| Mapped to Repbase | 97,036 |
| No hit | 40,394,271 |

Seqseq: sequenced sequences

Figure 2:
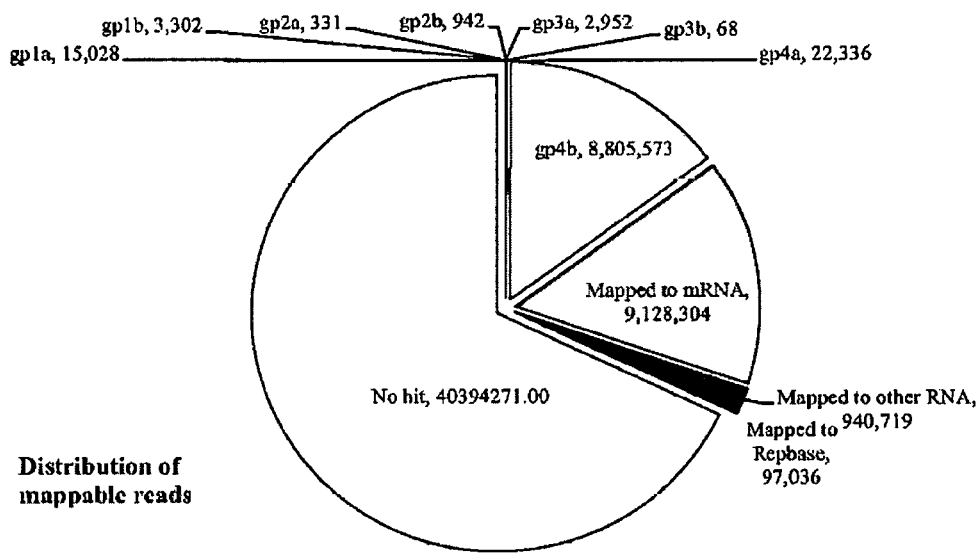
FIG. 2 shows the distribution of mappable reads

Mapping of reads was carried out following the schematic in FIG. 5 where reads were either mapped or un-mapped to selected mirs and miRs in MiRbase. Interestingly, a large fraction of reads mapped to mRNA in the culture media. The distribution of all mappable reads is illustrated in FIG. 2. Of the mappable sequences, 385 mapped to known bovine miRNAs (Group 1a) and 87 mapped to known miRs of selected mammalian species in miRbase (Group 1b) but were considered novel to bovine (Table 5). Within selected mammalian species, 4 sequences mapped to known mirs in addition to mapping to the bovine genome within a predicted hairpin (Group 2a) and 128 sequences mapped to known mirs that mapped to the bovine genome but were not within a predicted hairpin (Group 2b). A total of 508 sequences mapped to known mirs and miRs of selected species but did not map to the bovine genome (Group 3a). In Group 3b, 73 sequences were identified that did not map to miRs but to mirs of selected species and did not map to the bovine genome. An additional group of 211 sequences were un-mappable to miRbase but were mapped to the bovine genome within regions that are predicted to form hairpins. Taken together, the sequencing data revealed the presence of known bovine miRNAs, miRNAs known in other mammalian species novel to bovine as well as sequences that are previously unidentified bovine-specific miRNAs.

TABLE 5

Classification of Mappable Sequences in IVF culture media

| | Group | # of Unique miRs |
|---|---|---|
| Known miRs | | |
| of Bos Taurus | Group 1a | 385 |
| of selected species | Group 1b | 87 |
| Predicted miRs | | |
| Mapped to known mirs of selected species and genome; within hairpins | Group 2a | 4 |

TABLE 5-continued

Classification of Mappable Sequences in IVF culture media

| | Group | # of Unique miRs |
|---|---|---|
| Mapped to known mirs of selected species and genome; no hairpins | Group 2b | 128 |
| Mapped to known mirs and miRs of selected species but unmapped to bovine genome | Group 3a | 508 |
| Mapped to known mirs of selected species but unmapped to bovine genome | Group 3b | 73 |
| Unmapped to known miRs but mapped to bovine genome and within hairpins | Group 4a | 211 |
| Overall (Unique mirs and miRs) | | 1,244 |

Differential Expression of miRNAs in Culture Media

After mapping, the number of read copies for each sample was normalized for comparison of expression between blastocyst conditioned media, degenerate conditioned media as well as the control SOF media which was never in contact with an embryo but was cultured in the same petri dish. Differential expression is representative of the mean normalized reads followed by a paired t-test of data across media generated from 3 replicates of IVF experiments. Analysis revealed 11 miRNAs that were differentially expressed between degenerate and blastocyst conditioned media (Table 6). The differentially expressed miRNAs were all more highly expressed in degenerate media compared to blastocyst media and consisted of both known mirs and miRs specific to bovine, swine, and predicted miRs that mapped to the bovine genome and were within a predicted hairpin forming sequence. Between control SOF media and blastocyst conditioned media, 8 miRNAs were differentially expressed and all were more highly expressed in control SOF media and were of either known bovine or swine sequences. Comparing degenerate conditioned media to SOF media, 4 miRNAs were differentially expressed where 2 were expressed higher in degenerate media and 2 were expressed higher in the control SOF media (Table 6).

TABLE 6

Summary of mean reads of miRNA sequences in culture media

| Comparison | Mean Reads ± SD | | Higher Expression (p-value) | Sequence |
|---|---|---|---|---|
| Degenerate (D) vs Blastocyst (B) | D | B | | |
| bta-mir-2887 | 7 ± 7 | 5 ± 5 | D (p <0.001) | GGTGCGGAGAGCCCTTCGTCCCGGGA (SEQ ID No.: 1) |
| bta-miR-24-3p | 9 ± 4 | 2 ± 1 | D (p <0.01) | TGGCTCAGTTCAGCAGGAAC (SEQ ID No.: 2) |
| ssc-miR-22 | 54 ± 52 | 27 ± 22 | D (p <0.02) | AAGCTGCCAGTTGAAGAACTGT (SEQ ID No.: 3) |
| PC-3p-21760 | 12 ± 17 | 7 ± 10 | D (p <0.02) | TTCCCGGAGTCGGGTTGCTT (SEQ ID No.: 4) |
| ssc-miR-423-5p | 12 ± 11 | 8 ± 7 | D (p <0.02) | TGAGGGGCAGAGAGCGAGACTTT (SEQ ID No.: 5) |
| bta-miR146a | 21 ± 29 | 6 ± 8 | D (p <0.02) | TGAGAACTGAATTCCATAGGTT (SEQ_ID No.: 6) |
| bta-miR-191 | 90 ± 75 | 20 ± 10 | D (p <0.03) | CAACGGAATCCCAAAAGCAGCTG (SEQ ID No.: 7) |
| bta-mir-2904 | 7 ± 7 | 2 ± 2 | D (p <0.03) | CCTCGGATAGCCGGTCCCCCGCC (SEQ ID No.: 8) |
| bta-miR-186 | 20 ± 19 | 9 ± 9 | D (p <0.04) | CAAAGAATTCTCCTTTTGGGCT (SEQ ID No.: 9) |
| bta-miR-148a | 94 ± 93 | 25 ± 18 | D (p <0.05) | TCAGTGCACTACAGAACTTTGT (SEQ ID No.: 10) |
| bta-miR-192 | 11 ± 13 | 2 ± 2 | D (p <0.05) | CTGACCTATGAATTGACAGCC (SEQ ID No.: 11) |
| SOF (S) vs Blastocyst (B) | S | B | | |
| ssc-let-7g | 13 ± 12 | 2 ± 2 | S (p <0.003) | TGAGGTAGTAGTTTGTACAGTT (SEQID No.: 43) |
| bta-miR-98 | 10 ± 11 | 0 ± 0 | S (p <0.006) | TGAGGTAGTAAGTTGTATTGTT (SEQ ID No.: 44) |
| bta-miR-374a | 6 ± 5 | 0 ± 0 | S (p <0.006) | TTATAATACAACCTGATAAGT (SEQID No.: 45) |
| bta-miR30a-5p | 20 ± 14 | 5 ± 5 | S (p <0.02) | TGTAAACATCCTCGACTGGAAGCT (SEQ ID No.: 46) |
| bta-mir-451 | 20 ± 13 | 0 ± 0 | S (p <0.02) | AAACCGTTACCATTACTGAGT (SEQ ID No.: 47) |
| bta-miR-125a | 88 ± 66 | 22 ± 17 | S (p <0.04) | TCCCTGAGACCCTTTAACCTGTG (SEQ ID No.: 48) |
| bta-miR-151-5p | 43 ± 37 | 6 ± 6 | S (p <0.05) | TCGAGGAGCTCACAGTCTAGT (SEQID No.: 49) |
| bta-miR-24-3p | 39 ± 30 | 2 ± 1 | S (p <0.05) | TGGCTCAGTTCAGCAGGAAC (SEQ ID No.: 50) |

TABLE 6-continued

Summary of mean reads of miRNA sequences in culture media

| Comparison | Mean Reads ± SD | | Higher Expression (p-value) | Sequence |
|---|---|---|---|---|
| Degenerate (D) vs SOF (S) | D | S | | |
| bta-miR-200a | 5 ± 5 | 0 ± 0 | D (p <0.007) | TAACACTGTCTGGTAACGATGT (SEQ ID No.: 51) |
| PC-3p-1296 | 5 ± 2 | 11 ± 13 | S (p <0.021) | ATTCCCCCTTTCCCGTGG (SEQ ID No.: 52) |
| bta-miR-27a-3p | 4 ± 5 | 10 ± 11 | S (p <0.03) | TTCACAGTGGCTAAGTTCCGC (SEQ ID No.: 53) |
| PC-3p-725 | 126 ± 19 | 105 ± 12 | D (p <0.04) | CCACCACGTTCCCGAGG (SEQ ID No.: 54) |

Figure 3:
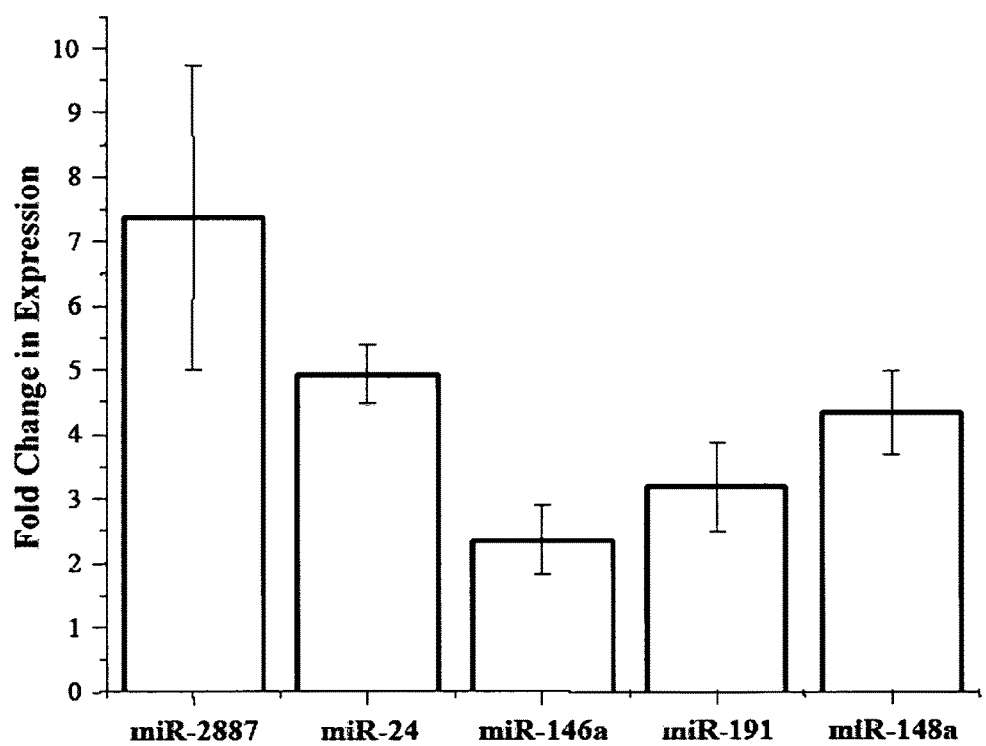
FIG. 3 shows gene expression validation of miRNA differentially expressed in degenerate media compared to blastocyst media. Error bars represent the expression range calculated as the fold change in expression using the SE of the mean fold change. Differential expression was confirmed for miR-24, miR-191 and miR-148a (P<0.05) which were more highly expressed in degenerate media compared to blastocyst media, while miR-146a and miR-2887 tended to be different (P<0.07).

PC: sequences in group4a that are not in miRbase, map to the bovine genome and are predicted to form hairpins Gene Expression Validation To confirm the sequencing results, miRNAs that were found to be significantly differentially expressed (P<0.05) between blastocyst and degenerate media were selected for validation of expression by qRT-PCR. The miRNAs selected were mir-2887, miR-24, miR146a, miR-191, and miR-148a and were tested within new biological replicates of media pools generated in 3 additional IVF experiments. Expression analysis confirmed 3 miRNAs, miR-24, miR-191 and miR-148a to be more highly expressed in degenerate conditioned media compared to blastocyst conditioned media, while miR-146a and miR-2887 tended to be differentially expressed (P<0.07). The fold difference in expression between degenerate and blastocyst conditioned media for miR-2887, miR-24, miR-146a, miR-191 and miR-148a was 7.4±2.4 SE (P=0.07), 4.9±0.5 SE (P<0.004), 2.4±0.5 SE (P=0.06), 3.2±0.7 SE (P<0.05) and 4.3±0.6 SE (P<0.05), respectively (FIG. 3). Thus, the expression of these miRNAs detected by qRT-PCR confirms the miRNA-seq results.

Supplementation of miR-24 to IVF Culture Media Reduces Embryonic Development and Represses its Target Gene CDKN1b To assess whether the presence of miRNA in the media affects embryonic development, a mimic of miR-24 was supplemented to the IVF culture media on day 5 of development corresponding to the morula stage. MiR-24 was chosen as it was more highly expressed in degenerate and control media compared to blastocyst media suggesting that the miRNA moves into the embryo or is degraded within the blastocyst media. Additionally, miR-24 is highly conserved across mammalian species and has been found to target mRNAs relating to cell proliferation and apoptosis. The miR-24 mimic supplemented to the media was a synthetic double-stranded RNA, similar in nature to endogenous miRNA. Across 3 IVF replicates, morula-stage embryos cultured in the presence of miR-24 mimic had a development rate of 48.3% compared to controls where 75.6% of the morula developed to the blastocyst stage (Table 2). This significant decline in embryonic development (P<0.0001; chi-square) as a result of supplementation of synthetic miR-24 suggests that the extracellular miRNA milieu greatly impacts the development of the embryo.

MiR-24 expression was profiled to understand expression across the stages of development in control embryos to better understand how alterations at differing time points may affect the embryo. Expression of miR-24 was significantly greater (fold change 4.6±0.1 SE, P<0.02; one-way ANOVA) in morula stage embryos in comparison to blastocyst stage embryos. In contrast, the expression of miR-24 in degenerate embryos was highly variable, reflecting no significant differences between the morula or blastocyst stage. The expression profile suggests that miR-24 becomes downregulated from the morula stage to the blastocyst stage where perhaps alterations in the gene regulation at this time point could lead to embryo growth arrest.

Figure 4:
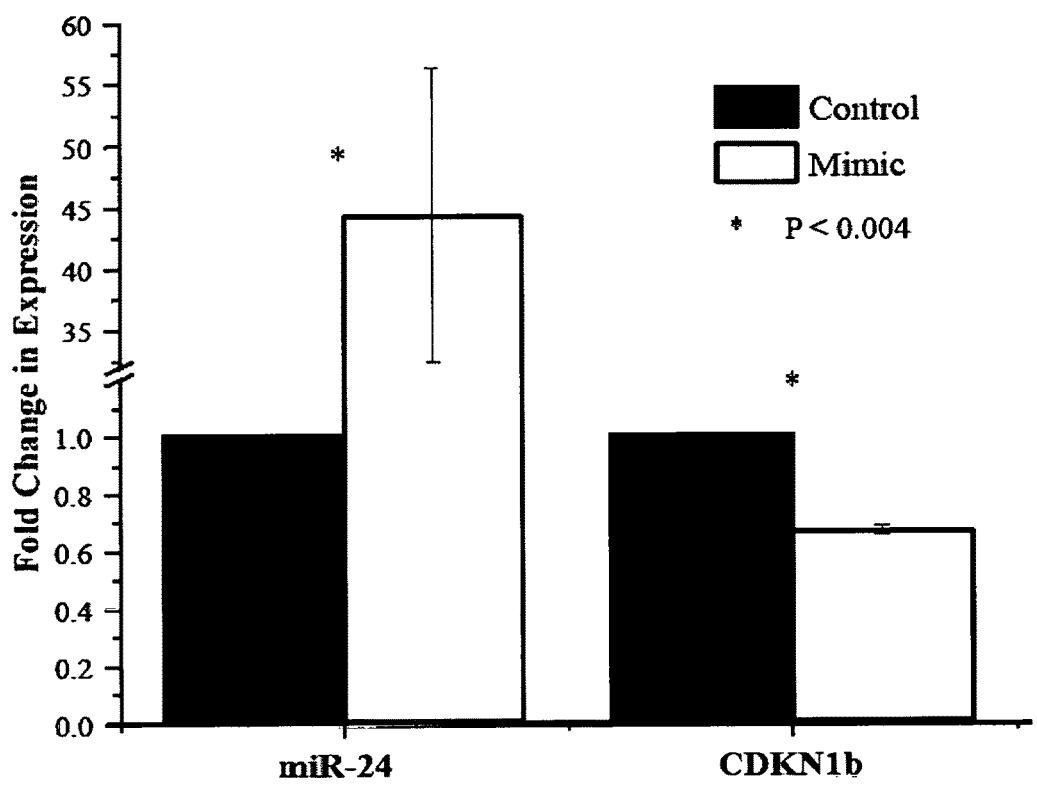
FIG. 4 shows that miR-24 in the media increases miR-24 expression in embryos and represses its mRNA target, CDKN1b. Fold change in expression of miR-24 and CDKN1b in control blastocysts versus mimic blastocysts. Error bars represent the expression range calculated as the fold change in expression using the SE of the mean fold change. Asterisk denotes statistical significance (*P<0.004)

To better understand the mechanisms by which supplementation of mimic miR-24 affects embryonic development, expression levels of miR-24 and its target gene CDKN1b were assessed in embryos cultured with the mimic. As illustrated in FIG. 4, blastocyst embryos cultured in the presence of mimic miR-24 more highly expressed miR-24 by 44.3±11.8 SE fold (P<0.004) compared to control cultured blastocysts. Additionally, expression of a target mRNA of miR-24, CDKN1b, a cell cycle regulator, was significantly reduced in mimic blastocysts by 33% compared to that of control blastocysts (fold change 0.7±0.01 SE; P<0.004; FIG. 4). Overall, increased presence of miR-24 in the extracellular environment leads to higher expression of miR-24 within embryos and results in decreased expression of miR-24's mRNA target.

DISCUSSION

It has been shown that the presence of miRNA in the culture media of IVF-produced embryos can be used as biomarkers of embryo quality. A differentially expressed miRNA, miR-24, was profiled within the embryo where its expression was found to be highly regulated throughout development, and addition of a mimic of miR-24 to the extracellular environment not only reduced development but also increased expression within the embryo and repressed expression of its target CDKN1b gene within embryos.

Deep-sequencing resulted in the detection of many miRNA sequences in the media. A large portion of the mappable miRNA was of known bovine miRs expected with recent advances in annotating bovine miRNA. Other sequences mapped to both predicted and known mir and miRs in other species including swine and human matches suggesting that further annotation of bovine miRNA is warranted. Indeed, a great number of sequences detected in the media were not identified in miRbase but mapped to the bovine genome and were within sequences predicted to form hairpins. These sequences are potentially novel bovine sequences that are yet to be characterized in terms of annotation and function, including roles in embryonic development within culture media. Interestingly, these sequences were significantly detected across multiple IVF biological replicates suggesting that they are not arbitrary to a particular IVF experiment and functionally are relevant to embryo development.

MiRNA spectra greatly differ between degenerate and blastocyst conditioned media. Both Kropp et al. [25] and Rosenbluth et al. [26] have previously identified miRNAs in the culture media, though the function of these miRNAs in the extracellular environment remained unknown. Differences in the regulation of the miRNA within the embryo alter the extracellular milieu. Several of the miRNA identified as differentially expressed miRNA regulate genes associated with cellular proliferation. For example, overexpression of miR-146a is associated with an increase in cell proliferation in a p-ERK-dependent manner [30], and both miR-24 and miR-148a overexpression act to repress p27 thereby increasing cell proliferation [31, 32]. Conversely, miR-24 overexpression in human cancer cells results in increased apoptosis by downregulation of BCL-2, an antiapoptotic gene [33]. Thus, the antagonistic interplay of the mRNAs targeted by miRNAs within the embryo to promote or inhibit development is reflected by the miRNAs present in media conditioned by embryos of differing quality. Additionally, miR-148a, a differentially expressed miRNA, may affect epigenetic regulation within the embryo. A previous study demonstrated that the interplay between miR-148a and its target DNMT1 forms a negative regulatory feedback loop, in which overexpression of DNMT1 leads to hypermethylation of miR-148a promoter which in turn downregulates miR-148a expression [34]. Therefore, alterations in miRNA expression as a result of the IVF culture environment have the potential to alter embryonic development through epigenetic mechanisms such as DNA methylation.

MiRNAs present in the media may reflect abnormalities in development due to perturbations of the embryo's genetics. For example, both miR-146a and miR-191, both more highly expressed in the degenerate media in the present study, have also been associated with embryonic abnormalities. Jeon et al. [35] reported the genotypic combination of miR-146aCC/miR-196a2CC to be more frequent in chromosomally normal spontaneous aborted fetuses. Similarly, Rosenbluth et al. [26] found differential secretion into culture media of miR-191 by aneuploid embryos compared to normal euploid embryos. Determining whether the embryo's genomics such as genotype or epigenetics change the extracellular milieu, or conversely whether the extracellular environment induces changes to the embryo needs further examination.

Further exploration of miR-24 expression revealed that the interplay between miRNA expression within the embryo and the extracellular environment is complex. miR-24 expression within the embryo is tightly regulated across the stages of development. During the transition from the morula to a blastocyst, addition of miR-24 to the media significantly reduced development, increased expression of the miRNA in the embryo, and reduced the expression of the target CDKN1b mRNA. Overexpression of miR-24 represses CDKN1b, which is a cell cycle inhibitor, thereby promoting cell proliferation in several cancer cell lines [32]. In this study, cellular proliferation was not quantified; however, likely other targets of miR-24 may also be underlying cell proliferation and death. For instance, loss of miR-24 leads to upregulation of dihydrofolate reductase (DHFR), an s-phase enzyme that regulates the cell cycle, and subsequently induces neoplastic growth in immortalized cell lines [36]. Other mRNA targets of miR-24 likely also play a role in poor development. Upregulation of miR-24 reduces the expression of H2AX in terminally differentiated hematopoietic cells which causes these cells to be overly sensitive to DNA damage; thereby leading to cellular demise [37]. Moreover, exogenous overexpression of the miR cluster 23a-27-24 in bone suppressed osteoblast differentiation by repressing SAT2B which acts with RUNX2 [38]. Thus, alterations of the level of miR-24 within the embryo as a response to extracellular miR-24 concentration potentially perturb the expression of several key mRNAs and gene networks regulating development.

MiRNAs are both taken up as well as secreted by the embryo to alter the expression of miRNAs in IVF culture media. Gene expression changes observed in embryos cultured in the presence of a higher concentration of miR-24 suggest that miRNAs are taken up by these embryos from the media. Initial RNA-sequencing revealed that miR-24 expression was higher in both degenerate and SOF control media in comparison to blastocyst media; however, no difference was observed between the baseline SOF control and degenerate media. Alone the sequencing data suggests either up-take or degradation of miR-24 in blastocyst media. Following mimic supplementation it can be concluded that miRNAs present in IVF media are taken up by the developing embryo. Studies have exemplified miRNA uptake into cells from the extracellular environment [9, 39]. Indeed a study by Sohel et al. [39] demonstrated uptake of exosome-coupled miRNA from bovine follicular fluid into granulosa cells with a corresponding increase in endogenous miRNA in transfected cells and down-regulation of target genes of the exosome-coupled miRNA.

The former study by Sohel et al. [39] also demonstrates the role miRNAs have in cell-to-cell signaling. In this study, miR-200a was higher in degenerate media compared to the SOF control as well as blastocyst media. Interestingly, studies reported that miR-200a present in both human myometrial cells and in the mice uterine luminal epithelial cells can alter the uterine environment by repressing STAT5 which subsequently induces the expression of the progesterone metabolizing enzyme 20α-hydroxysteroid dehydrogenase [40, 41]. As this miRNA is secreted by a degenerate embryo it could potentially act as a maternal recognition factor to alter progesterone levels signaling the presence of an abnormal embryo thereby preventing implantation. Characterization of the function of these miRNAs at the maternal-fetal interface is warranted in the future.

The regulatory nature of miRNAs makes these gene products of great interest to study in embryonic development, as underlying genomics, dictated by reprogramming and epigenetics, drives the embryo through the stages of development. The targets and functions of miRNAs should be further characterized in the embryo itself as well as the media in the future. Differences in the extracellular environment may provide a non-invasive method of surveying a single embryo for developmental competence based on the miRNA present. Current methods rely on morphology of the embryo, though it is known that embryos of similar morphology can de developmentally dissimilar [6, 42]. Furthermore, expression of miR-24 was reported to be lower in in vivo derived porcine embryos compared to in vitro derived embryos suggesting culture conditions alter miR expression within embryos [43]. Indeed it is known that bovine in vivo produced embryos are superior to in vitro produced embryos in terms of developmental potential though morphologically similar; thus miRNA expression in the media reflecting the genetics underlying development is a potential biomarker of development. It is known that the IVF process incurs changes to the embryo's transcriptome, where miRNA mimics and/or inhibitors supplemented to media provide another molecular tool to alter the underlying genetics or provide gene therapy.

Example 2 Small mRNA as Biomarkers for Embryo Viability Assays

Materials and Methods
In Vitro Production of Embryos
Embryos were generated through an IVF system as similarly described in Kropp et al. (2014). In brief, ovaries were obtained from a local slaughter house and oocytes were aspirated from 2-8 mm follicles. Cumulus-oocyte complexes were washed twice in Vigro TL-Hepes (Bioniche, Putman, Wash.) supplemented with gentamicin, sodium pyruvate and 3% fatty-acid free bovine serum albumin (FAF-BSA). Cohorts of 10 cumulus-oocyte complexes were then placed into a 50 µl drop of maturation medium composed of M-199 supplemented with 10% fetal bovine serum, sodium pyruvate, gentamicin, and gonadotropins (LH and FSH) and estradiol. Following 24 hours of incubation in maturation media, cumulus-oocyte complexes were removed from the media washed once in supplemented TL-Hepes and transferred to fresh 44 µl drops of IVF-TL medium (Millipore, Phillipsburg, N.J.) supplemented with FAF-BSA, sodium pyruvate and gentamicin. Sperm was prepared using a percoll gradient procedure as described in Parrish et al. (1995). The final concentration of sperm was adjusted to 1 million sperm/ml and added at a volume of 2 µl along with 2 µl of PHE and 2 µl of heparin to each fertilization media drop. The timing of fertilization was initiated Day 0 and gametes were co-incubated for 24 hours. Presumptive zygotes were then removed from fertilization medium on day 1, washed in supplemented TL-Hepes, and then were vortexed to strip away their cumulus cells. The presumptive zygotes were then transferred in cohorts of 25 to fresh 50 µl drops of synthetic oviductal fluid (SOF) culture media (Millipore, Phillipsburg, N.J.) supplemented with FAF-BSA, sodium pyruvate, amino acids, and gentamicin.

Embryos were cultured until day 5 of development where they were morphologically assessed and those demonstrating characteristics of the morula stage were washed and individually transferred to a fresh drop of SOF media lacking FAF-BSA supplementation. These embryos were culture until day 8 individually at which point they were morphologically assessed and those were deemed either a blastocyst or a degenerate embryo (those which fail to develop from the morula stage). Mid- and expanded blastocysts of quality grades 1-3 were collected and pooled together and media derived from these embryos was also collected and pooled together. Likewise, both degenerate embryos and their respective media was collected and pooled together. A total of 3 IVF replicates were carried out where 1 pool of embryos and media were collected per embryo type and replicate. Additionally, a different sire was used for each replicate to eliminate a bull effect.

RNA Extraction
RNA was extracted from media samples using the miRNAeasy Serum/Plasma kit (Qiagen, Germantown, Md.) which is designed to isolate cell-free total RNA. The input volume of media for extraction was 200 µl per sample where multiple extractions were carried out to achieve input requirements for small-RNA sequencing.

Library Preparation and Small-RNA Sequencing
Total RNA samples were processed by LC Sciences (Houston, Tex.). The library for each sample was prepared using the Illumina TruSeq™ Small RNA Library Prep kit following the kit's guidelines. The prepared library was then clustered on Illumina's Cluster Station followed by sequencing on an Illumina GAIIx instrument.

RNA-Sequencing Data Analysis
Sequencing data was analyzed using LC Sciences proprietary pipeline. The raw sequenced reads were extracted, filtered and those which were between 15-32 nucleotides in length were clustered into families and deemed unique sequences (family of raw sequencing reads with the same sequence). Reads were then mapped to the bovine UMD_3.1 reference genome. The total read fragments for each gene was then summed. Normalization of the reads and differential expression analysis was carried out in EdgeR using a negative binomial distribution to conduct a paired t-test. Significance was set at $p<0.05$.

Differential Expression Validation by Real-Time Quantitative PCR (qRT-PCR)
A subset of significantly differentially expressed mRNA fragments in the media were chosen to be validated both technically through qRT-PCR and biologically in pools of media derived from 4 additional IVF experiments. The total RNA was extracted from each pool as described above with the addition of a spike-in control, *C. elegans* miR-39. This control can be used a reference allowing quantification of expression following qRT-PCR. The extracted RNA was then reverse transcribed into cDNA using a MiScript II RT kit (Qiagen). The HiFlex buffer was used for subsequent quantification of both mRNA and mature miRNA (the spike-in control). The cDNA reaction adds a universal tag sequence to the 5' end which is necessary for subsequent steps to quantify these small fragments using the Qiagen PCR system. To assess gene expression, qRT-PCR was carried out using the miScript SYBR Green kit (Qiagen). A universal reverse primer in addition to a forward primer that is specifically designed to the sequence by Qiagen using their algorithms for small RNA was used; sequences are listed in a Table 7 below. The qRT-PCR reactions were carried in a Bio-Rad iCycler under the following conditions: 95° C. for 15 minutes followed by 40 cycles of 94° C. for 15 s, 55° C. for 30 s, and 70° C. for 30 s. Data was then analyzed using a paired t-test on the ΔCt values (Ct of mRNA-Ct of miR-39 spike-in control) for each mRNA. The fold change in expression was calculated used the $2^{-\Delta\Delta Ct}$ method as described by Livak and Schmittgen (2001).

TABLE 7

Primer Sequences used for qRT-PCR

| Gene | Primer Sequence (5'-3') |
| --- | --- |
| VSNL-1 | UGCUUGGACUACAUAUG (SEQ ID No.: 40) |
| POSTN | UUGGUUGAGGGUUGUA (SEQ ID No.: 41) |
| miR-39* | UCACCGGGUGUAAAUCAGCUUG (SEQ ID No.: 42) |

*C. elegans miR-39 Spike-in Control

Results
Small-RNA sequencing data revealed about 9,128,304 total reads mapped to mRNA across the media samples. For each gene the number of reads was summed for each sample and differential expression was analyzed. A total of 18 mRNAs were differentially expressed between blastocyst and degenerate media (Table 8). To further confirm the sequencing result, 2 of these mRNAs were further tested for differential expression through qRT-PCR in samples generated in 4 IVF experiments. Expression of small mRNA fragments corresponding to VSNL-1 and POST genes was confirmed as more highly expressed in blastocyst conditioned media compared to degenerate conditioned media. The fold changes in expression For VSNL-1 and POST were 3.14±1.10 SE ($p<0.05$) and 5.74±2.16 SE ($p<0.05$), respectively. Further validation of other mRNA fragments is currently underway.

Evidence from a study by Valadi et al. (2007) suggests that mRNAs contained with exosomes are secreted by mast cells former study identified full length transcripts while these are short fragments and their function is unknown. The genes that were highly differentially expressed and confirmed by qRT-PCR have potential roles in cell signaling. VSNL-1 encodes a calcium sensing protein and has been found to

TABLE 8

Differentially expressed mRNA in culture media

| Gene Symbol | Predominant Fragment Sequence | log2-fold-changes | Fold Change | p-value | Validated by qPCR |
| --- | --- | --- | --- | --- | --- |
| VSNL1 | TGCTTGGACTACATA (SEQ ID No.: 12) | -4.24 | 18.93 | 8.02E-005 | Y |
| LOC784070 | ACAACCTCAACTCCTA (SEQ ID No.: 13) | -5.86 | 58.19 | 9.17E-005 | |
| POSTN | TGGTTGAGGGTTGTA (SEQ ID No.: 14) | -6.28 | 77.93 | 2.81E-003 | Y |
| LOC504833 | CCACCTCGTTCCCGTGG (SEQ ID No.: 15) | -3.92 | 15.12 | 2.91E-003 | |
| RIC3 | ATAATTTTGAACGAAA (SEQ ID No.: 16) | -4.37 | 20.63 | 1.21E-002 | |
| KCTD12 | CCACCACGTTCTCGTGT (SEQ ID No.: 17) | -5.52 | 45.99 | 1.49E-002 | |
| LARS2 | ACCCGGGTGTCCCCTCCA (SEQ ID No.: 18) | -3.18 | 9.09 | 1.78E-002 | |
| NDST2 | CCGCCACGTCCCGTGG (SEQ ID No.: 19) | -3.89 | 14.78 | 1.82E-002 | |
| FSCN3 | CGCTGTGGGATGAACCA (SEQ ID No.: 20) | -4.15 | 17.80 | 2.16E-002 | |
| DLL4 | CCCCCACCTTCCCGTGG (SEQ ID No.: 21) | -3.70 | 12.97 | 2.68E-002 | |
| LOC785098 | CACCACGTTCCCGTGT (SEQ ID No.: 22) | -2.45 | 5.46 | 2.97E-002 | |
| NETO2 | AGAACTTGAAGGACCG (SEQ ID No.: 23) | 3.26 | 0.10 | 3.33E-002 | |
| ZNIF319 | CGGCCCTGGCGGAGCGC (SEQ ID No.: 24) | 2.35 | 0.20 | 3.60E-002 | |
| NAT12 | CCTCCGTTGCCCTCAGCC (SEQ ID No.: 25) | 3.67 | 0.08 | 4.20E-002 | |
| GCLC | CCCGGGTGTCCCCTCCA (SEQ ID No.: 26) | -3.78 | 13.76 | 4.28E-002 | |
| DAGLB | TCCCGGCCGATGCACCA (SEQ ID No.: 27) | -2.83 | 7.13 | 4.28E-002 | |
| ARCC1 | CACCACGTTCACGTGG (SEQ ID No.: 28) | -2.02 | 4.06 | 4.34E-002 | |
| LOC783819 | GCGGTCGGCGTCCCC (SEQ ID No.: 29) | 3.15 | 0.11 | 4.81E-002 | |

Interestingly the mRNA fragments identified here all contain an RNA binding protein motif within the short sequence. It is plausible that these mRNA fragments may be protected by proteins and hence are not degraded so these are detected within the media. The exact mechanism by which these small mRNAs are released from cells whether it be within exosomes or protein bound is unknown. It could be that they are degraded spliced fragments secreted or it could be that they have a function outside of the cell.

modulate calcium signaling within the central nervous system. Conversely, POSTN is a gene that is thought to facilitate heparin binding and cell adhesion. A more thorough understanding of their role in the media is needed, however, the data reveals consistency in expression across multiple IVF replicates suggesting that they have strong potential as biomarkers of development.

REFERENCES

1. Chandra A, Copen C, Stephen E. Infertility and Impaired Fecundity in the U.S.-1982-2010 Data from the National Health Survey of Family Growth. In: CDC; 2014.
2. Lucy M C. ADSA Foundation Scholar Award—Reproductive loss in high-producing dairy cattle: Where will it end? Journal of Dairy Science 2001; 84:1277-1293.
3. Diskin M G, Murphy J J, Sreenan J M. Embryo survival in dairy cows managed under pastoral conditions. Animal Reproduction Science 2006; 96:297-311.
4. 2012 Assisted Reproductive Technology Fertility Clinics Success Rates Report. In; 2014.
5. Farin P W, Piedrahita J A, Farin C E. Errors in development of fetuses and placentas from in vitro-produced bovine embryos. Theriogenology 2006; 65:178-191.
6. Van Soom A, Mateusen B, Leroy J, De Kruif A. Assessment of mammalian embryo quality: what can we learn from embryo morphology? Reprod Biomed Online 2003; 7:664-670.
7. Driver A M, Penagaricano F, Huang W, Ahmad K R, Hackbart K S, Wiltbank M C, Khatib H. RNA-Seq analysis uncovers transcriptomic variations between morphologically similar in vivo- and in vitro-derived bovine blastocysts. Bmc Genomics 2012; 13.
8. Mitchell P S, Parkin R K, Kroh E M, Fritz B R, Wyman S K, Pogosova-Agadjanyan E L, Peterson A, Noteboom J, O'Briant K C, Allen A, Lin D W, Urban N, et al. Circulating microRNAs as stable blood-based markers for cancer detection. Proceedings of the National Academy of Sciences of the United States of America 2008; 105: 10513-10518.
9. Valadi H, Ekstrom K, Bossios A, Sjostrand M, Lee J J, Lotvall J O. Exosome-mediated transfer of mRNAs and microRNAs is a novel mechanism of genetic exchange between cells. Nature Cell Biology 2007; 9:654-U672.
10. Wang K, Zhang S L, Weber J, Baxter D, Galas D J. Export of microRNAs and microRNA-protective protein by mammalian cells. Nucleic Acids Research 2010; 38:7248-7259.
11. Chen X, Ba Y, Ma L J, Cai X, Yin Y, Wang K H, Guo J G, Zhang Y J, Chen J N, Guo X, Li Q B, Li X Y, et al. Characterization of microRNAs in serum: a novel class of biomarkers for diagnosis of cancer and other diseases. Cell Research 2008; 18:997-1006.
12. Turchinovich A, Weiz L, Langheinz A, Burwinkel B. Characterization of extracellular circulating microRNA. Nucleic Acids Research 2011; 39:7223-7233.
13. Rayner K J, Hennessy E J. Extracellular communication via microRNA: lipid particles have a new message. Journal of Lipid Research 2013; 54:1174-1181.
14. Xu L, Yang B F, Ai J. MicroRNA transport: A new way in cell communication. Journal of Cellular Physiology 2013; 228:1713-1719.
15. Wang Z F, Yao H, Lin S, Zhu X, Shen Z, Lu G, Poon W S, Xie D, Lin M C M, Kung H F. Transcriptional and epigenetic regulation of human microRNAs. Cancer Letters 2013; 331:1-10.
16. Filipowicz W, Bhattacharyya S N, Sonenberg N. Mechanisms of post-transcriptional regulation by microRNAs: are the answers in sight? Nature Reviews Genetics 2008; 9:102-114.
17. Ambros V. The functions of animal microRNAs. Nature 2004; 431:350-355.
18. Farh K K H, Grimson A, Jan C, Lewis B P, Johnston W K, Lim L P, Burge C B, Bartel D P. The widespread impact of mammalian microRNAs on mRNA repression and evolution. Science 2005; 310:1817-1821.
19. Lim L P, Lau N C, Garrett-Engele P, Grimson A, Schelter J M, Castle J, Bartel D P, Linsley P S, Johnson J M. Microarray analysis shows that some microRNAs down-regulate large numbers of target mRNAs. Nature 2005; 433:769-773.
20. Bartel D P. MicroRNAs: Genomics, biogenesis, mechanism, and function. Cell 2004; 116:281-297.
21. Tang F, Kaneda M, O'Carroll D, Hajkova P, Barton S C, Sun Y A, Lee C, Tarakhovsky A, Lao K Q, Surani M A. Maternal microRNAs are essential for mouse zygotic development. Genes & Development 2007; 21:644-648.
22. Tesfaye D, Worku D, Rings F, Phatsara C, Tholen E, Schellander K, Hoelker M. Identification and Expression Profiling of MicroRNAs During Bovine Oocyte Maturation Using Heterologous Approach. Molecular Reproduction and Development 2009; 76:665-677.
23. Hossain M M, Salilew-Wondim D, Schellander K, Tesfaye D. The role of microRNAs in mammalian oocytes and embryos. Animal Reproduction Science 2012; 134: 36-44.
24. Mondou E, Dufort I, Gohin M, Fournier E, Sirard M A. Analysis of microRNAs and their precursors in bovine early embryonic development. Molecular Human Reproduction 2012; 18:425-434.
25. Kropp J, Salih S M, Khatib H. Expression of microRNAs in bovine and human pre-implantation embryo culture media. Front Genet 2014; 5:91.
26. Rosenbluth E M, Shelton D N, Wells L M, Sparks A E T, Van Voorhis B J. Human embryos secrete microRNAs into culture media-a potential biomarker for implantation. Fertility and Sterility 2014; 101:1493-1500.
27. Parrish J J, Krogenaes A, Suskoparrish J L. Effect of Bovine Sperm Separation by either Swim-Up Or Percoll Method on Success of In-Vitro Fertilization and Early Embryonic-Development. Theriogenology 1995; 44:859-869.
28. Livak K J, Schmittgen T D. Analysis of relative gene expression data using real-time quantitative PCR and the 2(T)(-Delta Delta C) method. Methods 2001; 25:402-408.
29. Driver A M, Huang W, Kropp J, Penagaricano F, Khatib H. Knockdown of CDKN1C (p57(kip2)) and PHLDA2 Results in Developmental Changes in Bovine Pre-implantation Embryos. Plos One 2013; 8:10.
30. Xu B, Wang N, Wang X H, Tong N, Shao N, Tao J, Li P C, Niu X B, Feng N H, Zhang L H, Hua L X, Wang Z J, et al. MiR-146a suppresses tumor growth and progression by targeting EGFR pathway and in a p-ERK-dependent manner in castration-resistant prostate cancer. Prostate 2012; 72:1171-1178.
31. Guo S L, Peng Z, Yang X, Fan K J, Ye H, Li Z H, Wang Y, Xu X L, Li J, Wang Y L, Teng Y. miR-148a Promoted Cell Proliferation by Targeting p27 in Gastric Cancer Cells. International Journal of Biological Sciences 2011; 7:567-574.
32. Giglio S, Cirombella R, Amodeo R, Portaro L, Lavra L, Vecchione A. MicroRNA miR-24 promotes cell proliferation by targeting the CDKs inhibitors p27Kip1 and p16INK4a. Journal of Cellular Physiology 2013; 228: 2015-2023.
33. Srivastava N, Manvati S, Srivastava A, Pal R, Kalaiarasan P, Chattopadhyay S, Gochhait S, Dua R, Bamezai R N K. miR-24-2 controls H2AFX expression regardless of gene copy number alteration and induces apoptosis by targeting antiapoptotic gene BCL-2: a potential for therapeutic intervention. Breast Cancer Research 2011; 13.

34. Xu Q, Jiang Y, Yin Y, Li Q, He J, Jing Y, Qi Y T, Li W, Lu B, Peiper S S, Jiang B H, Liu L Z. A regulatory circuit of miR-148a1152 and DNMT1 in modulating cell transformation and tumor angiogenesis through IGF-IR and IRS1. Journal of Molecular Cell Biology 2013; 5:3-13.
35. Jeon Y J, Kim S Y, Rah H, Choi D H, Cha S H, Yoon T K, Lee W S, Shim S H, Kim N K. Association of the miR-146aC>G, miR-149T>C, miR-196a2T>C, and miR-499A>G Polymorphisms with Risk of Spontaneously Aborted Fetuses. American Journal of Reproductive Immunology 2012; 68:408-417.
36. Mishra P J, Song B, Wang Y, Humeniuk R, Banerjee D, Merlino G, Ju J F, Bertino J R. MiR-24 Tumor Suppressor Activity Is Regulated Independent of p53 and through a Target Site Polymorphism. Plos One 2009; 4.
37. Lal A, Pan Y F, Navarro F, Dykxhoorn D M, Moreau L, Meire E, Bentwich Z, Lieberman J, Chowdhury D. miR-24-mediated downregulation of H2AX suppresses DNA repair in terminally differentiated blood cells. Nature Structural & Molecular Biology 2009; 16:492-498.
38. Hassan M Q, Gordon J A R, Beloti M M, Croce C M, van Wijnen A J, Stein J L, Stein G S, Lian J B. A network connecting Runx2, SATB2, and the miR-23a similar to 27a similar to 24-2 cluster regulates the osteoblast differentiation program. Proceedings of the National Academy of Sciences of the United States of America 2010; 107: 19879-19884.
39. Sohel M M H, Hoelker M, Noferesti S S, Salilew-Wondim D, Tholen E, Looft C, Rings F, Uddin M J, Spencer T E, Schellander K, Tesfaye D. Exosomal and Non-Exosomal Transport of Extra-Cellular microRNAs in Follicular Fluid: Implications for Bovine Oocyte Developmental Competence. Plos One 2013; 8.
40. Williams K C, Renthal N E, Condon J C, Gerard R D, Mendelson C R. MicroRNA-200a serves a key role in the decline of progesterone receptor function leading to term and preterm labor. Proceedings of the National Academy of Sciences of the United States of America 2012; 109: 7529-7534.
41. Haraguchi H, Saito-Fujita T, Hirota Y, Egashira M, Matsumoto L, Matsuo M, Hiraoka T, Koga K, Yamauchi N, Fukayama M, Bartos A, Cha J, et al. MicroRNA-200a Locally Attenuates Progesterone Signaling in the Cervix, Preventing Embryo Implantation. Molecular Endocrinology 2014; 28:1108-1117.
42. Crosier A E, Farin P W, Dykstra M J, Alexander J E, Farin C E. Ultrastructural morphometry of bovine blastocysts produced in vivo or in vitro. Biology of Reproduction 2001; 64:1375-1385.
43. Stowe H M, Curry E, Calcatera S M, Krisher R L, Paczkowski M, Pratt S L. Cloning and expression of porcine Dicer and the impact of developmental stage and culture conditions on MicroRNA expression in porcine embryos. Gene 2012; 501:198-205.

---

What is claimed is:

1. A method for selectively implanting a bovine embryo cultured in a culture medium into a female bovine animal for further development, the method comprising
   a) extracting RNA from the culture medium containing the bovine embryo;
   b) detecting an expression level of the miRNA bta-miR-2887 which has SEQ ID NO: 1 in the extracted RNA;
   c) comparing the expression level of the miRNA in the culture medium to (i) the expression level of the miRNA in the culture medium containing degenerative embryos, or (ii) a previously established standard value of the expression level of the miRNA, and detecting that the expression level is decreased in the miRNA from the culture medium of step (a) and selecting an embryo from a culture medium whose expression level of mir-2887 is decreased;
   d) transferring the embryo into a female bovine for further development, whereby the transferred embryo has a higher likelihood of successful development compared to an embryo not subjected to the selection.

2. The method of claim 1, wherein detecting comprises converting the miRNA to DNA via performing reverse transcription and amplifying the DNA via performing a polymerase chain reaction.

3. The method of claim 1, wherein the embryo has been grown in the culture medium in vitro for at least about 3 days.

4. The method of claim 3, wherein the embryo has developed into a blastocyst.

5. The method of claim 1, wherein the embryo is formed from an oocyte that was fertilized by in vitro fertilization.

6. The method of claim 5, wherein the in vitro fertilization includes gamete co-cultivation.

* * * * *

SEQUENCE LISTING

```
<160> NUMBER OF SEQ ID NOS: 54

<210> SEQ ID NO 1
<211> LENGTH: 26
<212> TYPE: DNA
<213> ORGANISM: Bos taurus

<400> SEQUENCE: 1
ggtgcggaga gcccttcgtc ccggga                                          26

<210> SEQ ID NO 2
<211> LENGTH: 20
<212> TYPE: DNA
<213> ORGANISM: Bos taurus

<400> SEQUENCE: 2
tggctcagtt cagcaggaac                                                 20

<210> SEQ ID NO 3
<211> LENGTH: 22
<212> TYPE: DNA
<213> ORGANISM: Bos taurus

<400> SEQUENCE: 3
aagctgccag ttgaagaact gt                                              22

<210> SEQ ID NO 4
<211> LENGTH: 20
<212> TYPE: DNA
<213> ORGANISM: Bos taurus

<400> SEQUENCE: 4
ttcccggagt cgggttgctt                                                 20

<210> SEQ ID NO 5
```

```
<210> SEQ ID NO 5
<211> LENGTH: 23
<212> TYPE: DNA
<213> ORGANISM: Bos taurus

<400> SEQUENCE: 5 tgagggcag agagcgagac ttt                                      23

<210> SEQ ID NO 6
<211> LENGTH: 22
<212> TYPE: DNA
<213> ORGANISM: Bos taurus

<400> SEQUENCE: 6
tgagaactga attccatagg tt                                      22

<210> SEQ ID NO 7
<211> LENGTH: 23
<212> TYPE: DNA
<213> ORGANISM: Bos taurus

<400> SEQUENCE: 7
caacggaatc ccaaaagcag ctg                                     23

<210> SEQ ID NO 8
<211> LENGTH: 23
<212> TYPE: DNA
<213> ORGANISM: Bos taurus

<400> SEQUENCE: 8
cctcggatag ccggtccccc gcc                                     23

<210> SEQ ID NO 9
<211> LENGTH: 22
<212> TYPE: DNA
<213> ORGANISM: Bos taurus

<400> SEQUENCE: 9
caaagaattc tccttttggg ct                                      22

<210> SEQ ID NO 10
<211> LENGTH: 22
<212> TYPE: DNA
<213> ORGANISM: Bos taurus

<400> SEQUENCE: 10
tcagtgcact acagaacttt gt                                      22

<210> SEQ ID NO 11
<211> LENGTH: 21
<212> TYPE: DNA
<213> ORGANISM: Bos taurus

<400> SEQUENCE: 11
ctgacctatg aattgacagc c                                       21

<210> SEQ ID NO 12
<211> LENGTH: 15
<212> TYPE: DNA
<213> ORGANISM: Bos taurus

<400> SEQUENCE: 12
tgcttggact acata                                              15
```

```
<210> SEQ ID NO 13
<211> LENGTH: 16
<212> TYPE: DNA
<213> ORGANISM: Bos taurus

<400> SEQUENCE: 13
acaacctcaa ctccta                                                     16

<210> SEQ ID NO 14
<211> LENGTH: 15
<212> TYPE: DNA
<213> ORGANISM: Bos taurus

<400> SEQUENCE: 14
tggttgaggg ttgta                                                      15

<210> SEQ ID NO 15
<211> LENGTH: 17
<212> TYPE: DNA
<213> ORGANISM: Bos taurus

<400> SEQUENCE: 15
ccacctcgtt cccgtgg                                                    17

<210> SEQ ID NO 16
<211> LENGTH: 16
<212> TYPE: DNA
<213> ORGANISM: Bos taurus

<400> SEQUENCE: 16
ataattttga acgaaa                                                     16

<210> SEQ ID NO 17
<211> LENGTH: 17
<212> TYPE: DNA
<213> ORGANISM: Bos taurus

<400> SEQUENCE: 17
ccaccacgtt ctcgtgt                                                    17

<210> SEQ ID NO 18
<211> LENGTH: 18
<212> TYPE: DNA
<213> ORGANISM: Bos taurus

<400> SEQUENCE: 18
acccgggtgt cccctcca                                                   18

<210> SEQ ID NO 19
<211> LENGTH: 16
<212> TYPE: DNA
<213> ORGANISM: Bos taurus

<400> SEQUENCE: 19
ccgccacgtc ccgtgg                                                     16

<210> SEQ ID NO 20
<211> LENGTH: 17
<212> TYPE: DNA
<213> ORGANISM: Bos taurus

<400> SEQUENCE: 20
cgctgtggga tgaacca                                                    17
```

<210> SEQ ID NO 21
<211> LENGTH: 17
<212> TYPE: DNA
<213> ORGANISM: Bos taurus

<400> SEQUENCE: 21
cccccacctt cccgtgg                                                   17

<210> SEQ ID NO 22
<211> LENGTH: 16
<212> TYPE: DNA
<213> ORGANISM: Bos taurus

<400> SEQUENCE: 22
caccacgttc ccgtgt                                                    16

<210> SEQ ID NO 23
<211> LENGTH: 16
<212> TYPE: DNA
<213> ORGANISM: Bos taurus

<400> SEQUENCE: 23
agaacttgaa ggaccg                                                    16

<210> SEQ ID NO 24
<211> LENGTH: 17
<212> TYPE: DNA
<213> ORGANISM: Bos taurus

<400> SEQUENCE: 24
cggccctggc ggagcgc                                                   17

<210> SEQ ID NO 25
<211> LENGTH: 18
<212> TYPE: DNA
<213> ORGANISM: Bos taurus

<400> SEQUENCE: 25
cctccgttgc cctcagcc                                                  18

<210> SEQ ID NO 26
<211> LENGTH: 17
<212> TYPE: DNA
<213> ORGANISM: Bos taurus

<400> SEQUENCE: 26
cccgggtgtc ccctcca                                                   17

<210> SEQ ID NO 27
<211> LENGTH: 17
<212> TYPE: DNA
<213> ORGANISM: Bos taurus

<400> SEQUENCE: 27
tcccggccga tgcacca                                                   17

<210> SEQ ID NO 28
<211> LENGTH: 16
<212> TYPE: DNA
<213> ORGANISM: Bos taurus

<400> SEQUENCE: 28
caccacgttc acgtgg                                                    16

<210> SEQ ID NO 29
<211> LENGTH: 15
<212> TYPE: DNA
<213> ORGANISM: Bos taurus

<400> SEQUENCE: 29
gcggtcggcg tcccc                                                    15

<210> SEQ ID NO 30
<211> LENGTH: 26
<212> TYPE: RNA
<213> ORGANISM: Artificial Sequence
<220> FEATURE:
<223> OTHER INFORMATION: Primer Sequence

<400> SEQUENCE: 30
ggugcggaga gcccuucguc ccggga                                        26

<210> SEQ ID NO 31
<211> LENGTH: 22
<212> TYPE: RNA
<213> ORGANISM: Artificial Sequence
<220> FEATURE:
<223> OTHER INFORMATION: Primer Sequence

<400> SEQUENCE: 31
uggcucaguu cagcaggaac ag                                            22

<210> SEQ ID NO 32
<211> LENGTH: 24
<212> TYPE: RNA
<213> ORGANISM: Artificial Sequence
<220> FEATURE:
<223> OTHER INFORMATION: Primer Sequence

<400> SEQUENCE: 32
ugagaacuga auuccauagg uugu                                          24

<210> SEQ ID NO 33
<211> LENGTH: 23
<212> TYPE: RNA
<213> ORGANISM: Artificial Sequence
<220> FEATURE:
<223> OTHER INFORMATION: Primer Sequence

<400> SEQUENCE: 33
caacggaauc ccaaaagcag cug                                           23

<210> SEQ ID NO 34
<211> LENGTH: 22
<212> TYPE: RNA
<213> ORGANISM: Artificial Sequence
<220> FEATURE:
<223> OTHER INFORMATION: Primer Sequence

<400> SEQUENCE: 34
ucagugcacu acagaacuuu gu                                            22

<210> SEQ ID NO 35
<211> LENGTH: 22
<212> TYPE: RNA
<213> ORGANISM: Artificial Sequence
<220> FEATURE:
<223> OTHER INFORMATION: Primer Sequence

<400> SEQUENCE: 35
ucaccggrug uaaaucagcu ug                                    22

<210> SEQ ID NO 36
<211> LENGTH: 20
<212> TYPE: DNA
<213> ORGANISM: Artificial Sequence
<220> FEATURE:
<223> OTHER INFORMATION: Forward Primer

<400> SEQUENCE: 36
cccagaggac acgcatttgg                                       20

<210> SEQ ID NO 37
<211> LENGTH: 21
<212> TYPE: DNA
<213> ORGANISM: Artificial Sequence
<220> FEATURE:
<223> OTHER INFORMATION: Reversed Primer

<400> SEQUENCE: 37
aggagaggaa tcatctgcgg c                                     21

<210> SEQ ID NO 38
<211> LENGTH: 18
<212> TYPE: DNA
<213> ORGANISM: Artificial Sequence
<220> FEATURE:
<223> OTHER INFORMATION: Forward Primer

<400> SEQUENCE: 38
tgcccagaat atcatccc                                         18

<210> SEQ ID NO 39
<211> LENGTH: 18
<212> TYPE: DNA
<213> ORGANISM: Artificial Sequence
<220> FEATURE:
<223> OTHER INFORMATION: Reversed Primer

<400> SEQUENCE: 39
aggtcagatc cacaacag                                         18

<210> SEQ ID NO 40
<211> LENGTH: 17
<212> TYPE: RNA
<213> ORGANISM: Artificial Sequence
<220> FEATURE:
<223> OTHER INFORMATION: Primer Sequence

<400> SEQUENCE: 40
ugcuuggacu acauaug                                          17

<210> SEQ ID NO 41
<211> LENGTH: 16
<212> TYPE: RNA
<213> ORGANISM: Artificial Sequence
<220> FEATURE:
<223> OTHER INFORMATION: Primer Sequence

<400> SEQUENCE: 41
uugguugagg guugua                                           16

<210> SEQ ID NO 42
<211> LENGTH: 22

<212> TYPE: RNA
<213> ORGANISM: Artificial Sequence
<220> FEATURE:
<223> OTHER INFORMATION: Primer Sequence

<400> SEQUENCE: 42
ucaccgggug uaaaucagcu ug                                    22

<210> SEQ ID NO 43
<211> LENGTH: 22
<212> TYPE: DNA
<213> ORGANISM: Bos taurus

<400> SEQUENCE: 43
tgaggtagta gtttgtacag tt                                    22

<210> SEQ ID NO 44
<211> LENGTH: 22
<212> TYPE: DNA
<213> ORGANISM: Bos taurus

<400> SEQUENCE: 44
tgaggtagta agttgtattg tt                                    22

<210> SEQ ID NO 45
<211> LENGTH: 21
<212> TYPE: DNA
<213> ORGANISM: Bos taurus

<400> SEQUENCE: 45
ttataataca acctgataag t                                     21

<210> SEQ ID NO 46
<211> LENGTH: 24
<212> TYPE: DNA
<213> ORGANISM: Bos taurus

<400> SEQUENCE: 46
tgtaaacatc ctcgactgga agct                                  24

<210> SEQ ID NO 47
<211> LENGTH: 21
<212> TYPE: DNA
<213> ORGANISM: Bos taurus

<400> SEQUENCE: 47
aaaccgttac cattactgag t                                     21

<210> SEQ ID NO 48
<211> LENGTH: 23
<212> TYPE: DNA
<213> ORGANISM: Bos taurus

<400> SEQUENCE: 48
tccctgagac cctttaacct gtg                                   23

<210> SEQ ID NO 49
<211> LENGTH: 21
<212> TYPE: DNA
<213> ORGANISM: Bos taurus

<400> SEQUENCE: 49
tcgaggagct cacagtctag t                                     21

```
<210> SEQ ID NO 50
<211> LENGTH: 20
<212> TYPE: DNA
<213> ORGANISM: Bos taurus

<400> SEQUENCE: 50
tggctcagtt cagcaggaac                                               20

<210> SEQ ID NO 51
<211> LENGTH: 22
<212> TYPE: DNA
<213> ORGANISM: Bos taurus

<400> SEQUENCE: 51
taacactgtc tggtaacgat gt                                            22

<210> SEQ ID NO 52
<211> LENGTH: 18
<212> TYPE: DNA
<213> ORGANISM: Bos taurus

<400> SEQUENCE: 52 attcccctt tcccgtgg                                                  18

<210> SEQ ID NO 53
<211> LENGTH: 21
<212> TYPE: DNA
<213> ORGANISM: Bos taurus

<400> SEQUENCE: 53
ttcacagtgg ctaagttccg c                                             21

<210> SEQ ID NO 54
<211> LENGTH: 17
<212> TYPE: DNA
<213> ORGANISM: Bos taurus

<400> SEQUENCE: 54
ccaccacgtt cccgagg                                                  17
```